United States Patent
Ogasawara

(10) Patent No.: US 10,966,687 B2
(45) Date of Patent: Apr. 6, 2021

(54) ULTRASONIC DIAGNOSTIC APPARATUS

(71) Applicant: TOSHIBA MEDICAL SYSTEMS CORPORATION, Otawara (JP)

(72) Inventor: Yoichi Ogasawara, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 1067 days.

(21) Appl. No.: 14/794,359

(22) Filed: Jul. 8, 2015

(65) Prior Publication Data
US 2015/0305718 A1 Oct. 29, 2015

Related U.S. Application Data

(63) Continuation of application No. PCT/JP2014/051224, filed on Jan. 22, 2014.

(30) Foreign Application Priority Data

Jan. 23, 2013 (JP) .............................. JP2013-010265
Jan. 21, 2014 (JP) .............................. JP2014-008832

(51) Int. Cl.
*A61B 8/08* (2006.01)
*A61B 8/00* (2006.01)
*A61B 8/14* (2006.01)

(52) U.S. Cl.
CPC .............. *A61B 8/5207* (2013.01); *A61B 8/14* (2013.01); *A61B 8/4245* (2013.01);
(Continued)

(58) Field of Classification Search
CPC ........... A61B 8/00; A61B 8/08; A61B 8/0841; A61B 8/14; A61B 8/42; A61B 8/4245;
(Continued)

(56) References Cited

U.S. PATENT DOCUMENTS

2004/0019270 A1* 1/2004 Takeuchi ................. A61B 8/14
600/407
2005/0119569 A1 6/2005 Ohtake
(Continued)

FOREIGN PATENT DOCUMENTS

JP 2005-124712 A 5/2005
JP 2006-167267 A 6/2006
(Continued)

OTHER PUBLICATIONS

International Search Report dated Apr. 15, 2014 in PCT/JP2014/051224 filed Jan. 22, 2014 with English translation.
(Continued)

*Primary Examiner* — Carolyn A Pehlke
(74) *Attorney, Agent, or Firm* — Oblon, McClelland, Maier & Neustadt, L.L.P.

(57) ABSTRACT

According to one embodiment, an ultrasonic diagnostic apparatus includes an ultrasonic probe, position detector detecting a probe position, ultrasonic image generation circuitry generating an ultrasonic image, storage circuitry storing volume data and a designation position in association with each other, slice image generation circuitry generating a slice image to the designation position based on the data and the designation position, a display displaying at least one of first display displaying the slice image and the ultrasonic image and second display displaying contents different from contents in the first display, control circuitry controlling switching from the first display to the second display in response to movement of the probe position into a range to the designation position.

13 Claims, 21 Drawing Sheets

(52) U.S. Cl.
CPC ............ *A61B 8/4254* (2013.01); *A61B 8/461* (2013.01); *A61B 8/463* (2013.01); *A61B 8/466* (2013.01); *A61B 8/467* (2013.01); *A61B 8/469* (2013.01); *A61B 8/54* (2013.01); *A61B 8/483* (2013.01)

(58) Field of Classification Search
CPC ....... A61B 8/4254; A61B 8/461; A61B 8/463; A61B 8/465–469; A61B 8/54
See application file for complete search history.

(56) References Cited

U.S. PATENT DOCUMENTS

2012/0165671 A1\* 6/2012 Hill ...................... A61B 8/0883
600/443
2012/0262453 A1 10/2012 Endo et al.
2013/0018263 A1\* 1/2013 Kimoto ................... A61B 8/40
600/440

FOREIGN PATENT DOCUMENTS

| | | |
|---|---|---|
| JP | 3793126 B2 | 7/2006 |
| JP | 2011-125567 A | 6/2011 |
| WO | WO 2006/059668 A1 | 6/2006 |

OTHER PUBLICATIONS

Written Opinion dated Apr. 15, 2014 in PCT/JP2014/051224 filed Jan. 22, 2014.

\* cited by examiner

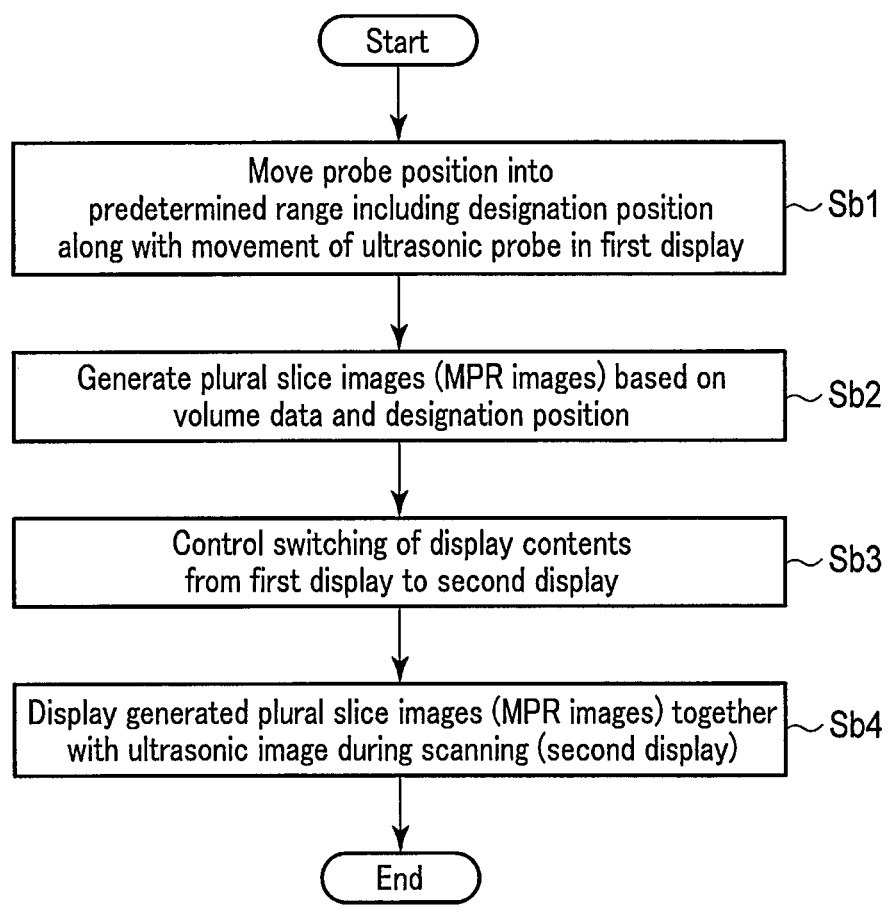
F I G. 14

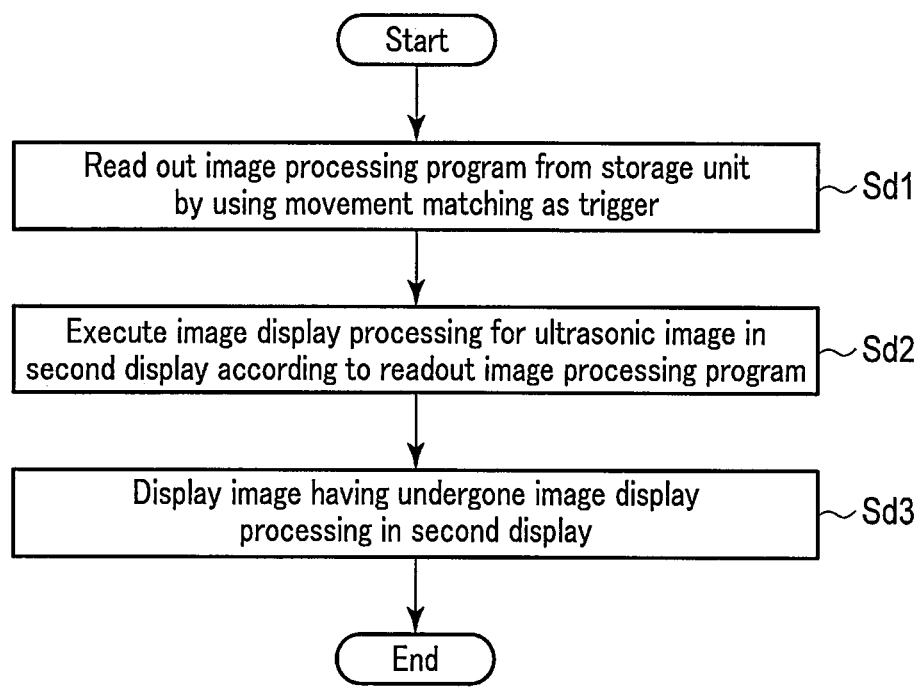
F I G. 20

ULTRASONIC DIAGNOSTIC APPARATUS

CROSS-REFERENCE TO RELATED APPLICATIONS

This application is a Continuation application of PCT Application No. PCT/JP2014/051224, filed Jan. 22, 2014 and based upon and claims the benefit of priority from the Japanese Patent Application No. 2013-010265, filed Jan. 23, 2013 and the Japanese Patent Application No. 2014-008832, filed Jan. 21, 2014, the entire contents of all of which are incorporated herein by reference.

FIELD

Embodiments described herein relate generally to an ultrasonic diagnostic apparatus.

BACKGROUND

In recent years, an ultrasonic diagnostic apparatus has a function of performing display (to be referred to as dual display hereinafter) of a tomographic image corresponding to a scanning slice by ultrasonic waves together with a B-mode image by using an output from a position sensor such as a magnetic sensor and three-dimensional image data collected by modalities such as an X-ray CT (Computed Tomography) apparatus and MRI (Magnetic Resonance Imaging) apparatus. FIG. 21 is a view showing an example of dual display. With dual display, differential diagnosis of a benign/malignant tumor by dynamic tumor observation using ultrasonically guided puncture and a contrast medium is efficiently and accurately performed. An ultrasonic diagnostic apparatus having a dual display function designates a specific position via an operation by an operator using position information of a position sensor. The ultrasonic diagnostic apparatus has a guide function of performing guide from a slice during scanning to the specific position in accordance with the distance between the slice during scanning and the specific position, and a direction perpendicular to the scanning slice.

The ultrasonic diagnostic apparatus having the guide function allows guide to a position with respect to the scanning slice including the specific position. However, there are an infinite number of scanning slices including the specific position. Therefore, the operator needs to confirm, in advance, a plurality of scanning slice candidates associated with puncture treatment among the plurality of scanning slices including the specific position. The plurality of scanning slice candidates include, for example, a slice where it is possible to grasp the running position of a lumen such as a blood vessel or bile duct positioned near a treatment target region, and a slice where it is possible to grasp the position of another tissue region adjacent to a tissue region when the treatment target region is close to the boundary of treatment target tissue. In addition, an advanced technique for reproducing the same scanning slice among the plurality of confirmed scanning slices is required for the operator.

To support recognition of the position of an ultrasonic scanning slice in a three-dimensional space, the ultrasonic diagnostic apparatus having the dual display function has an image processing function such as surface rendering using three-dimensional image data by a number of modalities, and a function of displaying a three-dimensional body mark indicating the current scanning slice by processing position information in real time. FIG. 22 is a view showing an example of a conventional three-dimensional body mark.

A three-dimensional body mark can indicate, to the operator, the relative position of an ultrasonic probe with respect to an object. However, it is impossible to efficiently guide a position, at which the ultrasonic probe is brought into contact with the object, to the position of the ultrasonic probe with respect to a scanning slice desired by the operator by only displaying the three-dimensional body mark. That is, displaying again the slice desired by the operator depends on the memory and skill of the operator. Thus, it takes time to reproduce the slice desired by the operator.

The conventional ultrasonic diagnostic apparatus can display, by ultrasonic scanning, a B-mode image which is almost the same as that stored in the past. When, however, the almost same B-mode image is displayed (to be referred to as almost same image display hereinafter), it is necessary to perform an input operation for displaying a plurality of screens by other modalities while holding the probe position in order to display a plurality of slice images by the other modalities, each of which includes a specific position, with respect to the displayed B-mode image. Consequently, in addition to the cumbersome operation, a display slice may deviate. In the conventional ultrasonic diagnosis apparatus, when almost same image display is executed, if another B-mode image such as a vertical slice including the specific position is generated, if various software programs associated with ultrasonic diagnosis are activated, or if a B-mode image in which an annotation about a slice image is displayed is displayed, it is necessary to perform an input operation such as an addition operation or scan condition change operation by an input device, and thus it may be impossible to display a desired slice while holding the probe position, as described above. That is, the operator needs to execute an input operation while maintaining a slice, resulting in cumbersomeness.

As described above, in the conventional ultrasonic diagnostic apparatus, when almost same image display is executed, the operator needs to execute again an input operation by the input device, thereby degrading the diagnosis efficiency.

BRIEF DESCRIPTION OF DRAWINGS

FIG. 14 is an example of a flowchart illustrating a procedure of switching the display contents of the display screen from the first display to the second display by using, as a trigger, the movement of the probe position into the predetermined range corresponding to the designation position according to the first modification of the first embodiment.

FIG. 20 is a flowchart illustrating an example of the procedure of image display processing according to the second embodiment.

DETAILED DESCRIPTION

Figure 1:
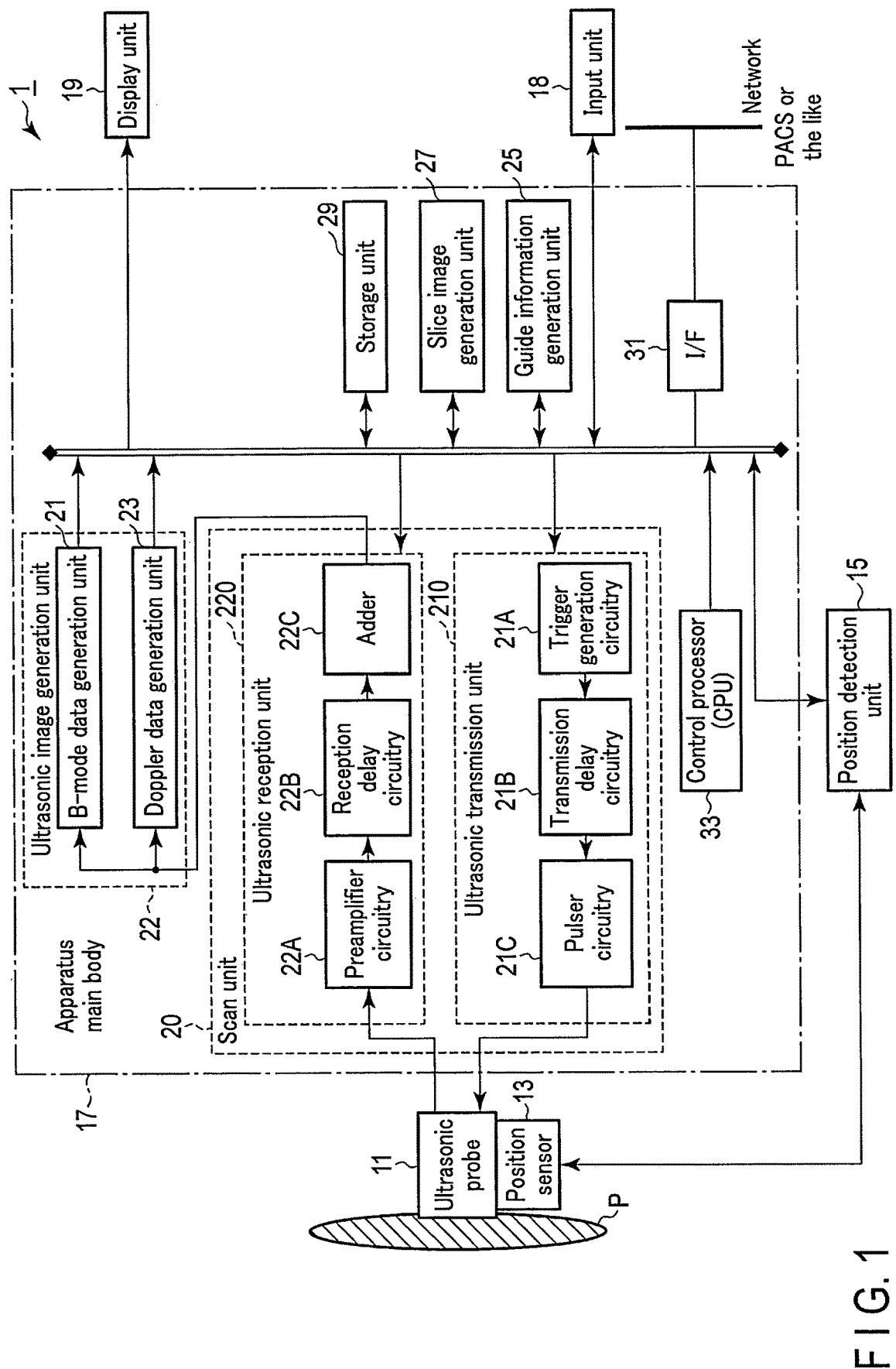
FIG. 1 is a view showing an example of the arrangement of an ultrasonic diagnostic apparatus according to the first embodiment.

In general, according to one embodiment, an ultrasonic diagnostic apparatus includes an ultrasonic probe, a position detector, ultrasonic image generation circuitry, storage circuitry, slice image generation circuitry, a display and control circuitry.

The ultrasonic probe transmits an ultrasonic wave to an object and receives a reflected wave from the object.

The position detector detects a probe position of the ultrasonic probe.

The ultrasonic image generation circuitry generates an ultrasonic image based on the received reflected wave.

The storage circuitry stores acquired volume data about the object and a designation position designated by an operator in association with each other.

The slice image generation circuitry generates a scanning slice image corresponding to the designation position based on the volume data and the designation position.

The display displays at least one of first display of displaying the scanning slice image and the ultrasonic image and second display of displaying display contents different from display contents in the first display.

The control circuitry controls switching from the first display to the second display in response to movement of the probe position detected by the position detector into a range corresponding to the designation position.

The ultrasonic diagnostic apparatus according to an embodiment will be described below with reference to the accompanying drawings. Note that in the following description, the same reference numerals denote components having almost the same functions and arrangements, and a repetitive description thereof will be made, only as needed.

First Embodiment

FIG. 1 is a view showing the block arrangement of an ultrasonic diagnostic apparatus 1 according to the embodiment. As shown in FIG. 1, the ultrasonic diagnostic apparatus 1 includes an ultrasonic probe 11, a position sensor 13, a position detection unit 15, an apparatus main body 17, an input unit 18 which is connected to the apparatus main body 17 and used to load various kinds of instructions, commands, and information from an operator into the apparatus main body 17, and a display unit 19. In addition, the ultrasonic diagnostic apparatus 1 may be connected to a network and a bio-signal measuring device (not shown) represented by an electrocardiograph, phonocardiograph, sphygmograph, or respiration sensor via an interface (to be referred to as an I/F hereinafter) 31.

The ultrasonic probe 11 includes a plurality of piezoelectric transducers, a matching layer, and a backing material provided on the rear side of the plurality of piezoelectric transducers. The plurality of piezoelectric transducers are acoustoelectric reversible conversion elements such as piezoelectric ceramics. The plurality of piezoelectric transducers are juxtaposed and mounted on the distal end of the ultrasonic probe 11. Note that the following description will be provided based on the assumption that one piezoelectric transducer forms one channel. The piezoelectric transducer generates an ultrasonic wave in response to a driving signal supplied from an scan unit 20 (to be described later). When an ultrasonic wave is transmitted to an object P via the ultrasonic probe 11, the transmitted ultrasonic wave is reflected by a discontinuity surface of acoustic impedance of the living tissue of the object. The piezoelectric transducer receives the reflected ultrasonic wave (reflected wave), and generates an echo signal. The amplitude of the echo signal depends on an acoustic impedance difference on the discontinuity surface as a boundary by which the ultrasonic wave is reflected. The frequency of the echo signal generated when the transmitted ultrasonic wave is reflected by a moving blood flow or the surface of a cardiac wall or the like shifts depending on the velocity component of the moving body (the blood flow or the surface of the cardiac wall) in the ultrasonic transmission direction due to the Doppler effect.

The ultrasonic probe 11 will be described below as a probe for performing two-dimensionally scanning with a one-dimensional array. Note that the ultrasonic probe 11 may be a mechanical four-dimensional probe which executes three-dimensional scanning by swinging a one-dimensional array in a direction perpendicular to the array direction of the plurality of transducers. In addition, the ultrasonic probe 11 is not limited to a mechanical four-dimensional probe, and may be a two-dimensional array probe.

The matching layer is provided on the ultrasonic emitting surface side of the plurality of piezoelectric transducers to efficiently transmit/receive ultrasonic waves to/from the object P. The backing material prevents the ultrasonic waves from propagating backward from the piezoelectric transducers.

The position sensor 13 acquires position information of the ultrasonic probe 11 with reference to a predetermined reference position. The position information includes coordinate information indicating the position of the ultrasonic probe 11 with respect to the predetermined reference position and angle information about the angle of the ultrasonic probe 11. The angle information indicates, for example, the inclination of the ultrasonic probe 11 with reference to predetermined reference axes. The predetermined reference position is, for example, the position of the apparatus main body 17 of the ultrasonic diagnostic apparatus 1. Note that the reference position may be provided outside the apparatus main body 17. The predetermined reference axes are defined by, for example, two of preset three orthogonal axes and a straight line (to be referred to as a probe axis hereinafter) connecting the aperture center of the ultrasonic probe 11 and the center of gravity of the ultrasonic probe 11. Assume that the two axes are x- and y-axes of the three preset orthogonal axes (x-, y-, and z-axes). The position sensor 13 is provided in, for example, the ultrasonic probe 11. The position sensor 13 outputs the acquired position information to the position detection unit 15 (to be described later).

The position sensor 13 is, for example, a magnetic sensor, infrared sensor, angle sensor (for example, a gyro sensor), or the like. For example, the magnetic sensor acquires coordinate information with reference to the predetermined reference position by using the magnetism transmitted from a magnetic transmitter (not shown) in the position detection unit 15. The infrared sensor acquires coordinate information with reference to the predetermined reference position by using the infrared rays transmitted from an infrared transmitter (not shown) in the position detection unit 15. Note that more commonly used electromagnetic waves may be used instead of the infrared rays. Note that if the position sensor 13 is a magnetic sensor, the reference position may be the position of the magnetic transmitter. If the position sensor 13 is an infrared sensor, the reference position may be the position of the infrared transmitter. It is possible to adjust the reference position, as needed, in accordance with an instruction from the operator via the input unit 18 (to be described later). Note that the predetermined reference position may be a position at which the probe is brought into contact with the body surface of the object for the first time.

The angle sensor acquires angle information of the ultrasonic probe 11 around the predetermined reference axes. Note that the detected angle may be acquired based on the positions of two points output from two magnetic sensors, two infrared sensors, a combination of a magnetic sensor and infrared sensor, or the like provided on the side surface of the ultrasonic probe 11.

The position detection 15 detects the angles around the predetermined reference axes and three-dimensional coordinates indicating the position of the ultrasonic probe 11 with reference to the predetermined reference position by using the position information output from the position sensor 13. The detected three-dimensional coordinates and angle will be collectively referred to as a probe position hereinafter. More specifically, the position detection unit 15 determines three-dimensional coordinates indicating the position of the ultrasonic probe 11 and the angles around the reference axes on an absolute coordinate system with reference to the predetermined reference position. The position detection unit 15 outputs the probe position to CPU 33 and a guide information generation unit 25 (both of which will be described later).

The apparatus main body 17 includes the scan unit 20, an ultrasonic image generation unit 22, the guide information generation unit 25, a slice image generation unit 27, storage unit 29, the I/F 31, and the control processor (a central processing unit to be referred to as a CPU (control unit) hereinafter) 33.

The scan unit 20 generates a driving signal to drive each of the plurality of transducers in the ultrasonic probe 11. The scan unit 20 supplies the driving signal to each of the plurality of transducers. The scan unit 20 generates a reception signal based on a reception echo signal generated by each of the plurality of transducers. More specifically, the scan unit 20 includes an ultrasonic transmission unit 210 and an ultrasonic reception unit 220. The ultrasonic transmission unit 210 includes trigger generation circuitry 21A, transmission delay circuitry 21B, and pulser circuitry 21C. The ultrasonic reception unit 220 includes preamplifier circuitry 22A, reception delay circuitry 22B, and an adder 22C.

The trigger generation circuitry 21A repeatedly generates rate pulses for the formation of transmission ultrasonic waves at a predetermined rate frequency fr Hz (period, 1/fr sec). The trigger generation circuitry 21A repeatedly generates rate pulses at the predetermined rate frequency. The rate pulses are distributed to channels and sent to the transmission delay circuit 21B.

The transmission delay circuitry 21B gives each rate pulse a delay time (to be referred to as a transmission delay time hereinafter) necessary to focus transmission ultrasonic waves into a beam and determine transmission directivity for each of the plurality of channels. The storage unit 29 (to be described later) stores the transmission direction or transmission delay time (to be referred to as a transmission delay pattern hereinafter) of transmission ultrasonic waves. The CPU 33 refers to the transmission delay pattern stored in the storage unit 29 at the time of transmission of ultrasonic waves. The rate pulse given the delay time is sent to the pulser circuitry 21C (to be described later).

The pulser circuitry 21C applies a voltage pulse (driving signal) to each of the plurality of piezoelectric transducers of the ultrasonic probe 11 at the timing based on the rate pulse. With this operation, an ultrasonic beam is transmitted to the object.

An echo signal reflected by the living tissue of the object is captured as a reception echo signal via the ultrasonic probe 11 for each channel. The preamplifier circuitry 22A amplifies the reception echo signal from the object, captured via the ultrasonic probe 11, for each channel. An analog-to-digital converter (not shown) converts the amplified reception echo signal into a digital signal.

The reception delay circuitry 22B gives the reception echo signal converted into the digital signal a delay time (to be referred to as a reception delay time hereinafter) necessary to determine reception directivity. The storage unit 29 stores the reception direction or reception delay time (to be referred to as a reception delay pattern hereinafter) of the echo signal. The CPU 33 refers to the reception delay pattern stored in the storage unit 29.

The adder 22C adds a plurality of echo signals given delay times. With this addition operation, the ultrasonic receiver 220 generates a reception signal (to be also referred to as an RF (Radio Frequency) signal) whose reflection component from a direction corresponding to the reception directivity is enhanced. The transmission directivity and the reception directivity determine the comprehensive directivity of ultrasonic transmission/reception. This comprehensive directivity determines an ultrasonic beam (so-called "ultrasonic scanning line").

The ultrasonic reception unit 220 outputs a reception signal for each depth on each scanning line in a scanned region to B-mode data generation unit 21 or Doppler data generation unit 23 (to be described later). Note that the ultrasonic reception unit 220 may have a parallel reception function of simultaneously receiving echo signals generated on a plurality of scanning lines by one ultrasonic transmission operation.

The ultrasonic image generation unit 22 includes the B-mode data generation unit 21, the Doppler data generation unit 23, and a digital scan converter (to be referred to as a DSC hereinafter), image memory, and image combining device (none are shown).

The B-mode data generation unit 21 includes an envelope detector and a logarithmic converter (neither of which is shown). The envelope detector performs envelope detection of the reception signal output from the scan unit 20. The envelope detector outputs the envelope-detected signal to the logarithmic converter (to be described later). The logarithmic converter relatively enhances a weak signal by logarithmically converting the envelope-detected signal. The B-mode data generation unit 21 generates a signal value (B-mode data) for each depth on each scanning line based on the signal enhanced by the logarithmic converter.

If the ultrasonic probe 11 is a mechanical four-dimensional probe or two-dimensional array probe, the B-mode data generation unit 21 may generate three-dimensional B-mode data having a plurality of signal values respectively arrayed in the azimuth direction, elevation direction, and depth direction (to be referred to as the range direction hereinafter) in a scanned region. The range direction is the depth direction on a scanning line. The azimuth direction is, for example, an electronic scanning direction along the array direction of one-dimensional ultrasonic transducers. The elevation direction is the mechanical swinging direction of the one-dimensional ultrasonic transducers. Note that three-dimensional B-mode data may be data obtained by arraying a plurality of pixel values, a plurality of luminance values, or the like in the azimuth direction, elevation direction, and range direction, respectively, along scanning lines.

In addition, three-dimensional B-mode data may be data about an ROI preset in a scanned region. The B-mode data generation unit 21 may generate ultrasonic volume data instead of the three-dimensional B-mode data. The date generated by the B-mode data generation unit 21 will be collectively referred to as B-mode data hereinafter.

The B-mode data generation unit 21 associates the B-mode data with the absolute coordinate system by using the probe position detected by the position detection unit 15. Note that the B-mode data generation unit 21 may associate the probe position with the three-dimensional B-mode data.

The Doppler data generation unit 23 includes a mixer, low pass filter (to be referred to as an LPF hereinafter), and velocity/variance/power computation device (none are shown). The mixer multiplies the reception signal output from the scan unit 20 by a reference signal having a frequency $f_0$ equal to the transmission frequency. With this multiplication operation, a signal having a component with a Doppler shift frequency $f_d$ and a signal having a frequency component of $(2f_0+f_d)$ is obtained. The LPF removes a signal of a high-frequency component $(2f_0+f_d)$ from a signal having two types of frequency components from the mixer. The Doppler data generation unit 23 generates a Doppler signal having the component with the Doppler shift frequency $f_d$ by removing the signal of the high-frequency component $(2f_0+f_d)$.

Note that the Doppler data generation unit 23 may use a quadrature detection scheme to generate Doppler signals. In this case, a reception signal (RF signal) is quadrature-detected and converted into an IQ signal. The Doppler data generation unit 23 generates a Doppler signal having the component with the Doppler shift frequency $f_d$ by performing complex Fourier transform for the IQ signal. Doppler signals are, for example, Doppler components caused by a blood flow, tissue, and contrast medium.

The velocity/variance/power computation device includes an MTI (Moving Target Indicator) filter, LPF filter, and autocorrelation computation device (none are shown). Note that the device may include a cross-correlation computation device instead of the autocorrelation computation device. The MTI filter removes a Doppler component (a clutter component) caused by the respiratory movement or pulsatory movement of an organ or the like from a generated Doppler signal. The MTI filter is used to extract a Doppler component (to be referred to as a blood flow Doppler component hereinafter) concerning a blood flow from a Doppler signal. The LPF is used to extract a Doppler component (to be referred to as a tissue Doppler component hereinafter) concerning the movement of a tissue from a Doppler signal.

The autocorrelation computation device calculates an autocorrelation value with respect to a blood flow component and a tissue Doppler component. The autocorrelation computation device calculates the average velocity value, the variance, the reflection intensity (power) of the Doppler signal, and the like of the blood flow and tissue based on the calculated autocorrelation value. The velocity/variance/power computation device generates color Doppler data at each position in a predetermined region based on the average velocity value, the variance, the reflection intensity of the Doppler signal, and the like of the blood flow and tissue based on a plurality of Doppler signals. Doppler signals and color Doppler data will be collectively referred to as Doppler data hereinafter. Note that the Doppler data may be three-dimensional data (to be referred to as three-dimensional Doppler data hereinafter). Three-dimensional Doppler data and three-dimensional B-mode data will be collectively referred to as three-dimensional ultrasonic data hereinafter.

The ultrasonic image generation unit 22 generates a B-mode image based on the B-mode data generated by the B-mode data generation unit 21. The ultrasonic image generation unit 22 generates a Doppler image based on the Doppler data generated by the Doppler data generation unit 23. B-mode images and Doppler images will be collectively referred to as ultrasonic images hereinafter. That is, ultrasonic image generation unit 22 generates an ultrasonic image based on the data output from the scan unit 20.

More specifically, the ultrasonic image generation unit 22 executes coordinate conversion processing (resampling) for the DSC. Coordinate conversion processing is, for example, processing of converting a scanning line signal string for ultrasonic scanning, which is formed from B-mode data, Doppler data, and the like, into a scanning line signal string in a general video format represented by a TV format. The ultrasonic image generation unit 22 generates an ultrasonic image as a display image by coordinate conversion processing. More specifically, the ultrasonic image generation unit 22 generates a B-mode image based on the B-mode data. The ultrasonic image generation unit 22 generates a Doppler image such as an average velocity image, variance image, or power image based on the Doppler data.

The image memory stores data (to be referred to as image data hereinafter) corresponding to the generated ultrasonic images (B-mode images, average velocity images, variance images, and power images). The image data stored in the image memory is read out in accordance with an instruction from the operator via the input unit 18. The image memory is, for example, a memory which stores ultrasonic images corresponding to a plurality of frames immediately before freezing. Continuously displaying (cine displaying) the images stored in this cine memory can display a moving ultrasonic image on the display unit 19.

The image combining devise combines the ultrasonic image and a scanning slice image (to be described later) with the character information of various parameters, scale marks, and the like. The image combining device outputs the combined images to the display unit 19.

The guide information generation unit 25 generates probe guide information based on the probe position and a designation position (to be described later). The probe guide information is, for example, information displayed on the display unit 19 as a guide when the operator moves the ultrasonic probe 11 to the designation position. The guide information generation unit 25 updates the probe guide information along with the movement of the probe position. For example, the guide information generation unit 25 stores a program (to be referred to as a guide information generation program) for generating probe guide information in a memory (not shown). In this case, when a thumbnail image (to be described later) displayed on the display unit 19 is designated via an operation by the input unit 18 (to be referred to as a thumbnail designation operation hereinafter), the guide information generation unit 25 loads the guide information generation program into its own memory. Then, the guide information generation unit 25 generates probe guide information by operating the guide information generation program by using the probe position and designation position as input values.

The guide information generation unit 25 generates probe guide information based on a position corresponding to a slice designated with respect to the thumbnail image displayed on the display unit 19 and designated by the input unit 18, and the probe position detected by the position detection unit 15. The position corresponding to the designated slice is, for example, a position for defining a slice on the absolute coordinate system, or a probe position for acquiring an ultrasonic image corresponding to the slice.

Note that the guide information generation unit 25 may store a correspondence table of probe guide information for the probe position and designation position in the memory (not shown). In this case, when a thumbnail designation operation is executed, the guide information generation unit 25 may generate probe guide information based on the probe position, designation position, and correspondence table.

More specifically, when a thumbnail image displayed on the display unit 19 is designated via an operation by the input unit 18 (to be referred to as a thumbnail designation operation hereinafter), the guide information generation function 25 reads out, from the storage unit 29, a probe position (designation position) with respect to an ultrasonic image (upon collection) corresponding to the designated thumbnail image. The guide information generation unit 25 reads out the probe position of the ultrasonic probe 11 during scanning from the position detection unit 15 by using the thumbnail designation operation as a trigger.

The guide information generation unit 25 determines the distance (to be referred to as a guide distance hereinafter) between the designation position and the probe position with reference to the reference position based on the designation position read out from the storage unit 29 and the probe position read out from the position detection unit 15. The guide information generation unit 25 determines a direction (to be referred to as a guide direction hereinafter) from the probe position to the designation position based on the designation position read out from the storage unit 29 and the probe position read out from the position detection unit 15. More specifically, the guide information generation unit 25 calculates the guide distance and guide direction using the three-dimensional coordinates of the designation position and those of the probe position with reference to the reference position.

The guide information generation unit 25 determines the rotation angle of the ultrasonic probe 11 based on the designation position read out from the storage unit 29 and the probe position read out from the position detection unit 15. More specifically, the guide information generation unit 25 determines the rotation angle (to be referred to as a guide rotation angle hereinafter) of the ultrasonic probe 11 based on the angles around the reference axes at the designation position and the angles around the reference axes at the probe position. More specifically, the guide information generation unit 25 calculates, as a guide rotation angle, the absolute value of the angle difference between the angle at the designation position and that at the probe position for each of a plurality of reference axes. The probe guide information includes the guide distance, guide direction, and guide rotation angles.

Figure 2:
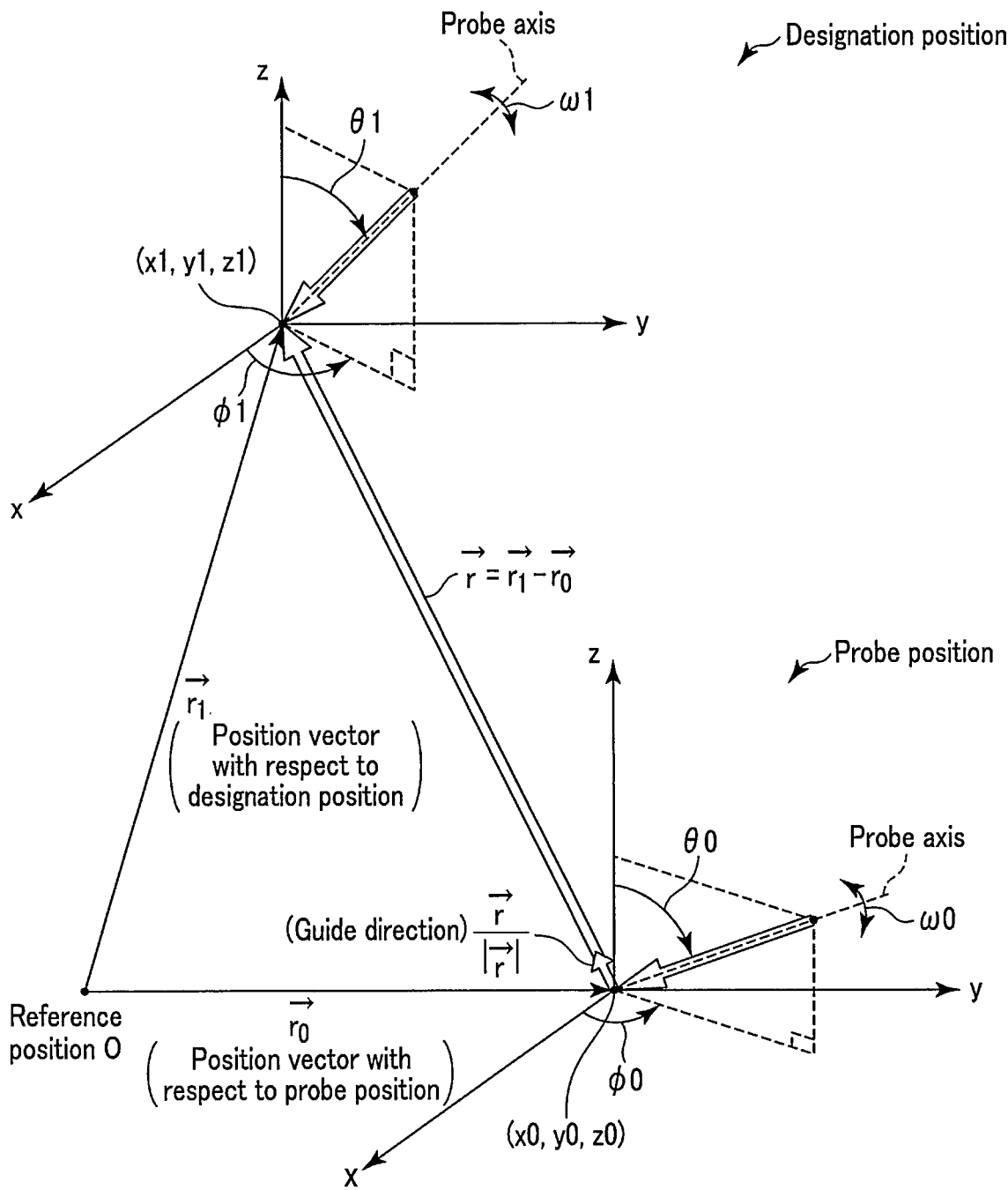
FIG. 2 is a schematic view showing an example of an overview of generation of probe guide information according to the first embodiment.

FIG. 2 is a schematic view showing an example of an overview of generation of probe guide information. As shown in FIG. 2, the probe position has, for example, the coordinates (x0, y0, z0) of the aperture center with respect to the reference position and angles ($\phi$0, $\theta$0, $\omega$0) around the reference axes (x-axis, y-axis, and probe axis). On the other hand, the designation position has, for example, the coordinates (x0, y0, z0) of the aperture center with respect to the reference position and the angles ($\phi$0, $\theta$0, $\omega$0) around the reference axes (x-axis, y-axis, and probe axis).

Referring to FIG. 2, for example, the guide distance is calculated by $((x1-x0)^2+(y1-y0)^2+(z1-z0)^2)^{(1/2)}$. As shown in FIG. 2, the guide direction is determined by, for example, calculating a direction vector from the probe position to the designation position. Referring to FIG. 2, the guide rotation angle around the Z-axis among the guide rotation angles is determined by calculating $|\phi1-\phi1|$. Referring to FIG. 2, the guide rotation angle around the x-axis among the guide rotation angles is determined by calculating $|\theta1-\theta0|$. Referring to FIG. 2, the guide rotation angle around the probe axis among the guide rotation angles is determined by calculating $|\omega1-\omega0|$.

Figure 3:
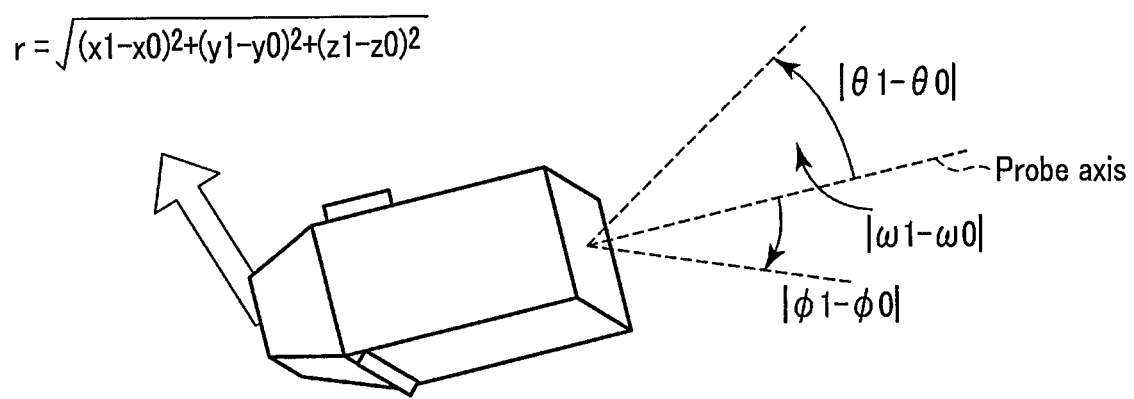
FIG. 3 is a view showing an example of display of the probe guide information according to the first embodiment.

FIG. 3 is a view showing an example of display of the probe guide information. As shown in FIG. 3, the probe guide information is displayed on the display unit 19 together with a schematic view (probe mark) about the ultrasonic probe 11. The formula of the probe guide information shown in FIG. 3 is stored in the memory (not shown) of the guide information generation unit 25 as, for example, the guide information generation program or correspondence table.

When an operation (to be referred to as a dual display operation hereinafter) of parallelly displaying an ultrasonic image and a slice image (to be referred to as a correspondence slice image hereinafter) corresponding to the ultrasonic image is input via the input circuitry 18, the slice image generation unit 27 generates the correspondence slice image based on the probe position and volume data stored in the storage unit 29. The correspondence slice image includes a scanned region with respect to the ultrasonic image. After the input of the dual display operation, the slice image generation unit 27 generates the slice image corresponding to the ultrasonic image updated according to the movement of the ultrasonic probe 11. That is, the slice position of the correspondence slice image and that of the ultrasonic image almost match each other.

The slice image generation unit 27 generates a three-dimensional body mark image indicating the probe mark and scanned region based on the probe position. The scanned region is superimposed on the body mark in a semitransparent or opaque state. Note that the slice image generation unit 27 may generate a three-dimensional body mark image based on the volume data and probe position by, for example, surface rendering processing or volume rendering processing. The slice image generation unit 27 outputs data about the ultrasonic image, correspondence slice image, and three-dimensional body mark image to the display unit 19.

When an instruction of a bookmark (to be referred to as a bookmark instruction hereinafter) is input via the input unit 18, the slice image generation unit 27 generates, based on an ultrasonic image (to be referred to as a bookmark image hereinafter) with respect to the bookmark instruction, a thumbnail image of a slice image corresponding to the bookmark image. The slice image generation unit 27 outputs the generated thumbnail image to the display unit 19. Note that the input unit 18 may input a slice designated by the operator in the volume data. In this case, the slice image generation unit 27 generates a thumbnail image corresponding to the input slice. For example, the thumbnail image is a thumbnail image of a correspondence slice image, and is, for example, an image obtained by reducing the correspondence slice image. Note that the thumbnail image may be an image obtained by resizing the correspondence slice image to a thumbnail size and correcting the resolution to be almost equal to that of the correspondence slice image.

When a thumbnail designation operation is executed, the slice image generation unit 27 generates an image (to be referred to as a 3DBM superimposed image hereinafter) by superimposing the probe guide information generated by the guide information generation unit 25 on the three-dimensional body mark image. A scanned region with respect to the designation position on the 3DBM superimposed image may be superimposed on the three-dimensional body mark in a semitransparent or opaque state. The slice image generation unit 27 outputs the 3DBM superimposed image to the display unit 19. Note that the slice image generation unit 27 updates the 3DBM superimposed image in accordance with the movement of the probe position.

Note that based on the volume data or ultrasonic image, the slice image generation unit 27 generates a thumbnail image with respect to the position corresponding to the slice designated via the input unit 18. More specifically, based on the volume data or ultrasonic image, the slice image generation unit 27 generates a thumbnail image with respect to the position corresponding to the designated slice using the probe position at the time of acquiring a position for defining the designated slice or an ultrasonic image including the designated slice. The slice image generation unit 27 outputs the generated thumbnail image to the display unit 19.

The storage unit 29 stores a plurality of reception delay patterns with different focus depths, a plurality of transmission delay patterns, apparatus control programs for the ultrasonic diagnostic apparatus 1, a diagnostic protocol, various data groups such as transmission/reception conditions, diagnosis information (patient IDs, findings by doctors, and the like), the reception signals generated by the scan unit 20, the B-mode data generated by the B-mode data generation unit 21, the Doppler data generated by the Doppler data generation unit 23, ultrasonic images (B-mode images, average velocity images, variance images, and power images), and the like.

The storage unit 29 stores volume data of the object acquired in the past by other modalities. For example, the volume data are transferred from other modalities (for example, an X-ray computed tomography apparatus, magnetic resonance imaging apparatus, and the like) capable of generating volume data or a medical image storage apparatus (not shown) to the storage unit 29 of the apparatus main body 17 via the I/F 31 and network. For the sake of simplicity, assume that the volume data is data generated by an X-ray computed tomography apparatus. When a dual display operation is input via the input unit 18, the storage unit 29 outputs the volume data to the slice image generation unit 27. Note that the volume data may be data generated by the ultrasonic diagnostic apparatus 1.

When a bookmark instruction is input via the input unit 18, the storage unit 29 stores, in association with the probe position, the correspondence slice image and ultrasonic image (bookmark image) which are displayed on the monitor. The probe position with respect to the ultrasonic image on which the bookmark instruction has been input corresponds to the above-described designation position. The stored correspondence slice image includes the scanned region with respect to the designation position. The correspondence slice image stored by the bookmark instruction will be referred to as a scanning slice image hereinafter. That is, a thumbnail image is a thumbnail of the scanning slice image. Note that the storage unit 29 may store the volume data and the position corresponding to the slice designated via the input unit 18 in association with each other.

The storage unit 29 stores the three-dimensional body mark, the probe mark, the marker indicating the scanned region, and the like. When a thumbnail designation operation is executed, the storage unit 29 outputs the three-dimensional body mark, the probe mark, the marker indicating the scanned region, and the like to the slice mage generation unit 27. Note that the storage unit 29 may store the guide information generation program. In this case, the storage unit 29 outputs the guide information generation program to the guide information generation unit 25 by using the input of the thumbnail designation operation as a trigger. The storage unit 29 also outputs the scanning slice image to the display unit 19 by using the thumbnail designation operation as a trigger.

The storage unit 29 stores a predetermined range. The predetermined range is used by the CPU 33 to determine that the designation position and the probe position almost match each other. The predetermined range is, for example, a range within a predetermined distance from the designation position. More specifically, the predetermined range is a range which includes the designation position and within which the guide distance is almost equal to zero. Also, the predetermined range is a range within which the guide rotation angles are almost equal to zero. That is, the predetermined range is a range for defining a range within which the designation position and the probe position almost match each other. Note that the storage unit 29 may store a predetermined threshold instead of the predetermined range. In this case, the predetermined threshold is a value such that the guide distance and guide rotation angles are almost equal to zero.

The I/F 31 is an interface for the network, and an external storage device and bio-signal measuring device (neither of which is shown). Data such as an ultrasonic image obtained by the apparatus main body 17, an analysis result, and the like can be transferred to another apparatus via the I/F 31 and the network.

The CPU 33 reads out the transmission delay pattern, reception delay pattern, and apparatus control program stored in the storage unit 29, based on the selection between the B mode and the Doppler mode, frame rate, scanned depth, transmission start/end, and the like which are input by the operator via the input unit 18, and controls the apparatus main body 17 in accordance with these piece of information.

When a dual display operation is input via the input unit 18, the CPU 33 controls the storage circuitry 29 and the slice image generation unit 27 to generate a correspondence slice image. In addition, the CPU 33 controls the display unit 19 to parallelly display the ultrasonic image and correspondence slice image.

When a bookmark instruction is input via the input unit 18 for the parallelly displayed ultrasonic image, the CPU 33 controls the storage unit 29 to store the bookmark image and correspondence slice image in association with the probe position. At this time, the CPU 33 controls the slice image generation unit 27 to generate a thumbnail image of a scanning slice image corresponding to the bookmark image.

When a thumbnail designation operation is input via the input unit 18, the CPU 33 controls the guide information generation unit 25 and slice image generation unit 27 to generate a 3DBM superimposed image. The CPU 33 outputs the scanning slice image corresponding to the designated thumbnail image from the storage unit 29 to the display unit 19 by using the thumbnail designation operation as a trigger. In addition, by using the thumbnail designation operation as a trigger, the CPU 33 controls the display unit 19 to parallelly display the scanning slice image and the ultrasonic image generated in real time. By using the thumbnail designation operation as a trigger, the CPU 33 controls the display unit 19 to display the 3DBM superimposed image together with the scanning slice image and the ultrasonic image generated in real time. Display of the scanning slice image, the ultrasonic image generated in real time, and the 3DBM superimposed image using the thumbnail designation operation as a trigger will be referred to as the first display hereinafter.

The CPU 33 reads out the predetermined range from the storage unit 29 by using the thumbnail designation operation as a trigger. When the probe position is moved into the predetermined range including the designation position along with the movement of the ultrasonic probe 11 (to be referred to as movement matching hereinafter), the CPU 33 controls the display unit 19 to display, on the display screen of the monitor of the display unit 19, predetermined display (to be referred to as movement matching display hereinafter) for notifying the operator of movement matching. The movement matching display indicates, for example, a character or icon for allowing the operator to recognize movement matching. Note that by using movement matching as a trigger, the CPU 33 may change at least one of the hue, brightness, and chroma of the probe mark on the 3DBM superimposed image so as to allow the operator to readily recognize movement matching. Furthermore, by using movement matching as a trigger, the CPU 33 may output a predetermined audio via a loudspeaker (not shown). The predetermined audio is an audio for allowing the operator to recognize movement matching. Note that by using movement matching as a trigger, the CPU 33 may control the display unit 19 to cancel display of the 3DBM superimposed image in the first display.

The input unit 18 is connected to the apparatus main body 17, and loads various kinds of instructions, commands, information, selections, and settings from the operator into the apparatus main body 17. The input unit 18 is implemented by input devices such as a trackball, switch buttons, mouse, and keyboard (none are shown). The input device detects the coordinates of the cursor displayed on the display screen and outputs the detected coordinates to the CPU 33. Note that the input device may be a touch panel provided to cover the display screen. In this case, the input unit 18 detects touched and instructed coordinates by a coordinate reading principle such as an electromagnetic induction scheme, a magnetostriction scheme, or a pressure sensitive scheme, and outputs the detected coordinates to the CPU 33. When the operator operates the end button or freeze button of the input unit 18, ultrasonic transmission/reception is terminated, and the apparatus main body 17 is set in a pause state.

Note that the input unit 18 may designate a slice of the object by an operator instruction. More specifically, the input unit 18 designates a slice for the volume data or ultrasonic image. The input unit 18 outputs a position corresponding to the designated slice to the storage unit 29. The input unit 18 designates a thumbnail image displayed on the display unit 19 by an operator instruction.

More specifically, the input unit 18 includes a dual display button for executing dual display, a bookmark button for inputting a bookmark instruction, a dial for selecting a plurality of thumbnail images displayed on the display unit 19, a trackball, and a cursor displayed on the display screen. The input unit 18 may include a determination button for designating a selected thumbnail image. Note that the bookmark button may be provided as a touch panel which covers the display screen of the display unit 19.

The input unit 18 operates the trackball or mouse to move the cursor displayed on the monitor of the display unit 19 onto, for example, one of the plurality of thumbnail images displayed on the display screen of the display unit 19. The input unit 18 designates the thumbnail image positioned behind the cursor by pressing the determination button. If a dial having a push switch is provided in the input unit 18, one of the plurality of thumbnail images is selected by rotation of the dial. At this time, when the push switch provided in the dial is pressed, the selected thumbnail image is designated.

The display unit 19 includes the monitor (not shown). The display unit 19 displays, on the monitor, various images generated by the ultrasonic image generation unit 22 and the slice image generation unit 27. The display unit 19 may execute adjustment such as brightness, contrast, dynamic range, or γ correction and assignment of a color map for the various images. More specifically, when a dual display operation is executed, the display unit 19 parallelly displays the correspondence slice image and ultrasonic image, and also displays the three-dimensional body mark image. Note that the display unit 19 may display a thumbnail image with respect to the position corresponding to the designated slice. When a thumbnail image is designated via the input unit 18, the display unit 19 displays probe guide information. Note that the display unit 19 may display the probe guide information together with at least one of the thumbnail image and the ultrasonic image.

Figure 4:
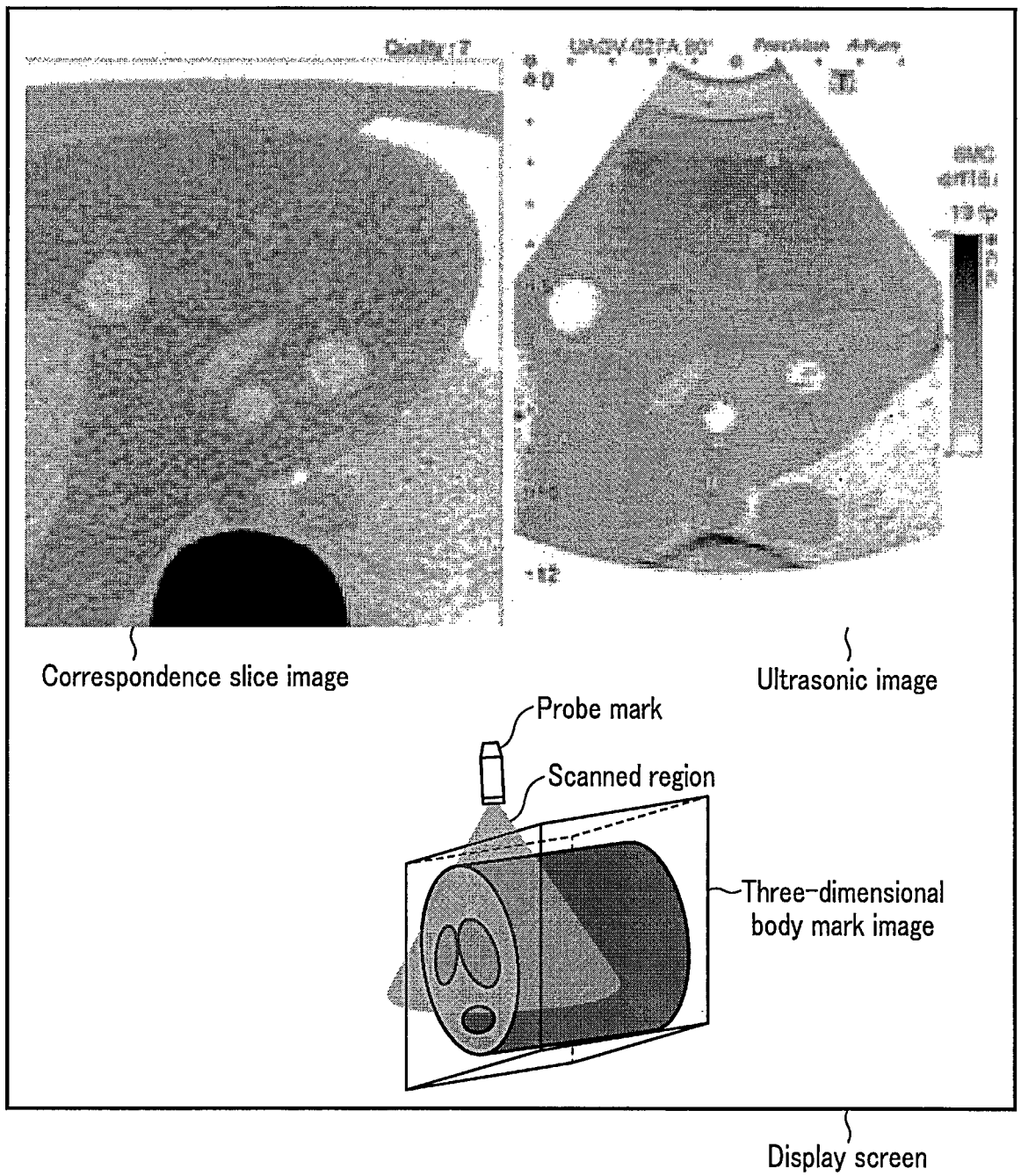
FIG. 4 is a view showing an example of a display screen on which an ultrasonic image and a correspondence slice image are displayed together with a three-dimensional body mark image according to the first embodiment.

FIG. 4 is a view showing a display example of the display screen on which the correspondence slice image and ultrasonic image are parallelly displayed and the three-dimensional body mark image is displayed. Note that the display unit 19 may parallelly display the correspondence slice image and ultrasonic image, and also display the three-dimensional body mark image and bookmark button.

Figure 5:
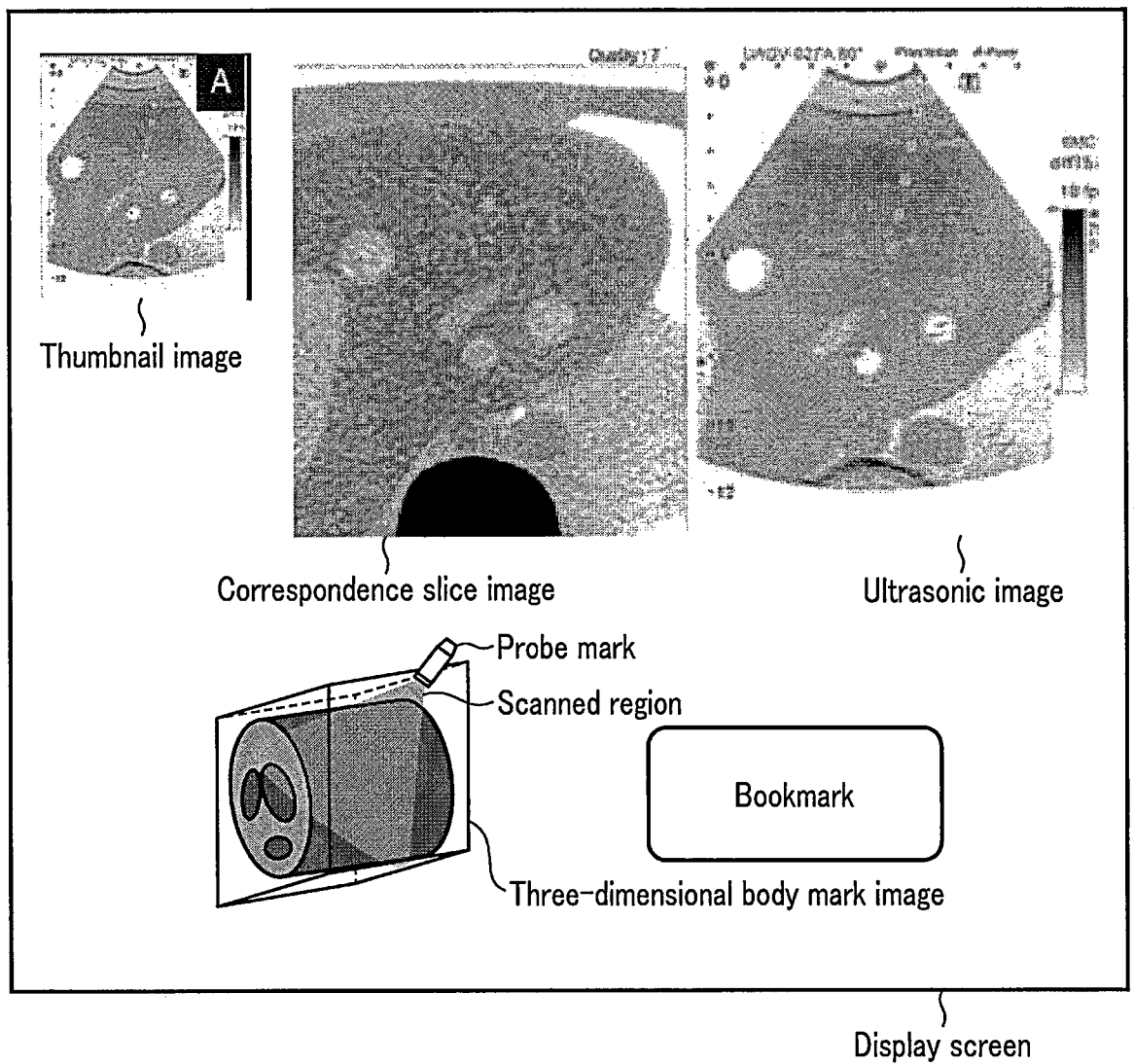
FIG. 5 is a view showing an example of the display screen when the ultrasonic image is bookmarked according to the first embodiment.
Figure 6:
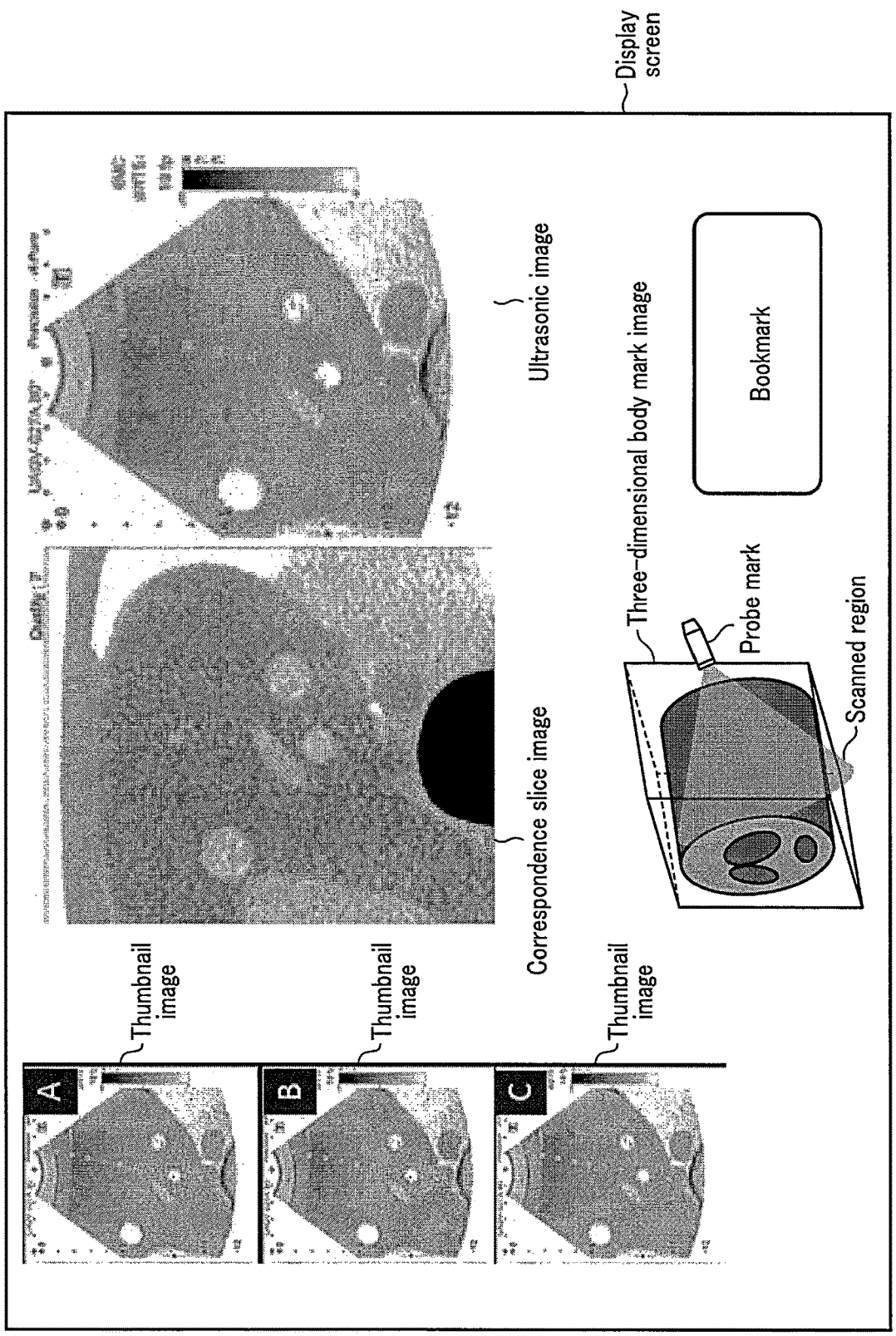
FIG. 6 is a view showing an example of the display screen when the third ultrasonic image is bookmarked according to the first embodiment.

When a bookmark instruction is input, the display unit 19 further displays the thumbnail image of the scanning slice image corresponding to the bookmark image. FIG. 5 is a view showing a display example of the display screen on which the ultrasonic image and correspondence slice image are parallelly displayed and the three-dimensional body mark image, the bookmark button, and a thumbnail image A are displayed. When a plurality of bookmark instructions are input via the input unit 18, the display unit 19 further displays a plurality of thumbnail images corresponding to the plurality of bookmark instructions. FIG. 6 is a view showing a display example of the display screen on which the ultrasonic image and correspondence slice image are parallelly displayed and the three-dimensional body mark image, the bookmark button, and the plurality of thumbnail images (A, B, and C) are displayed.

Figure 7:
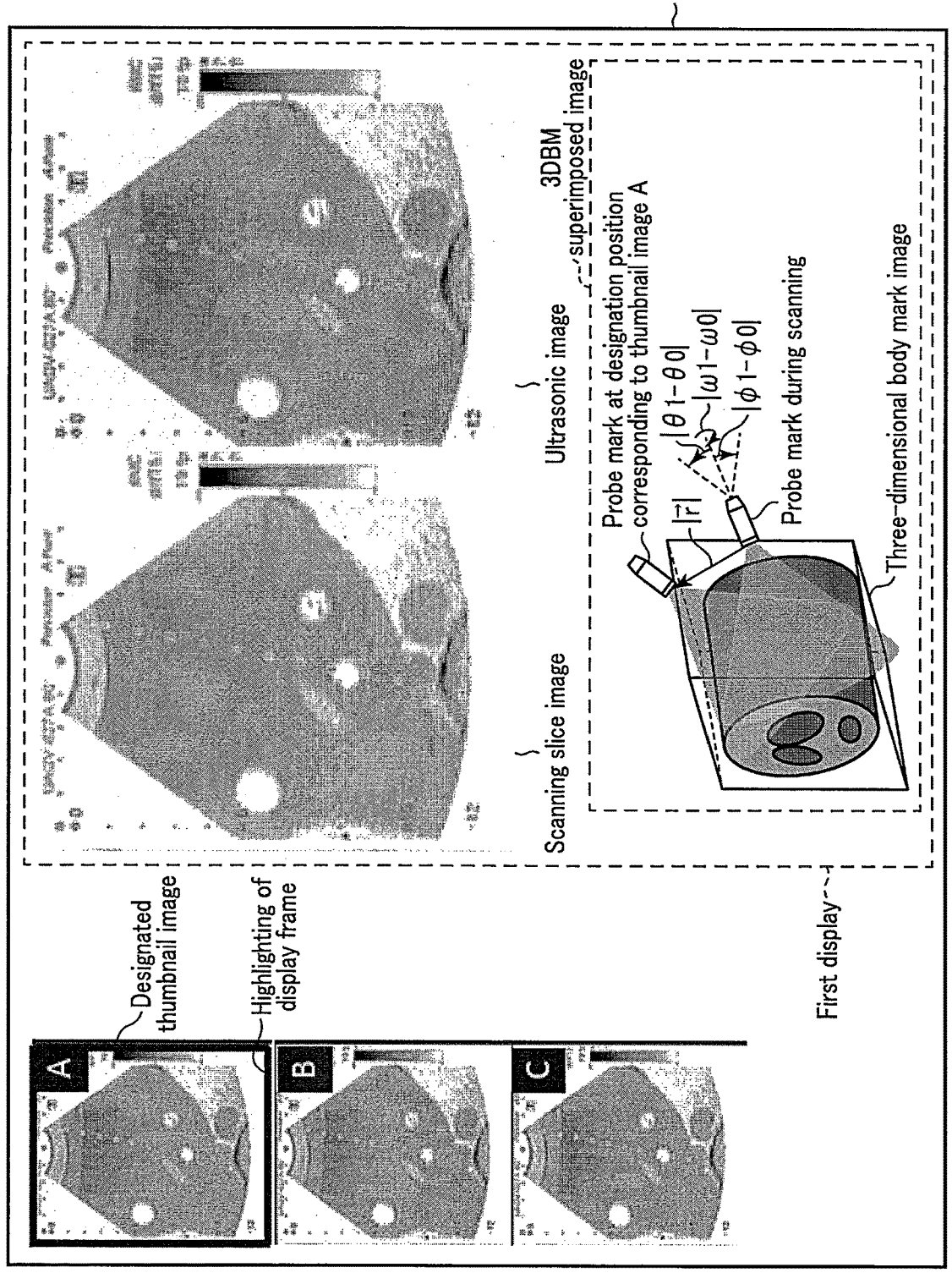
FIG. 7 is a view showing an example of the display screen when a thumbnail image is designated according to the first embodiment.

By using a thumbnail designation operation as a trigger, the display unit 19 replaces the correspondence slice image by a scanning slice image corresponding to a designated thumbnail image, and displays it. In addition, the display unit 19 replaces the three-dimensional body mark image by the 3DBM superimposed image. The display unit 19 highlights the display frame of the designated thumbnail image. FIG. 7 is a view showing an example in which the plurality of thumbnail images are displayed together with the first display. In the display shown in FIG. 7, the display unit 19 updates and displays probe guide information of the 3DBM superimposed image in accordance with the movement of the ultrasonic probe 11. Note that if there is no space to display the probe guide information on the display screen, the display unit 19 may set the probe guide information such as the numerical values of the angles and distance in FIG. 7 in a non-display state.

The display unit 19 displays the movement matching display using movement matching as a trigger. At the same time, the display unit 19 replaces the scanning slice image by the original correspondence slice image and displays it by using movement matching as a trigger. Note that the display unit 19 may cancel display of the probe guide information of the displayed 3DBM image by using movement matching as a trigger. Note that the display unit 19 may display the thumbnail images together with the ultrasonic image and guide information.

Figure 8:
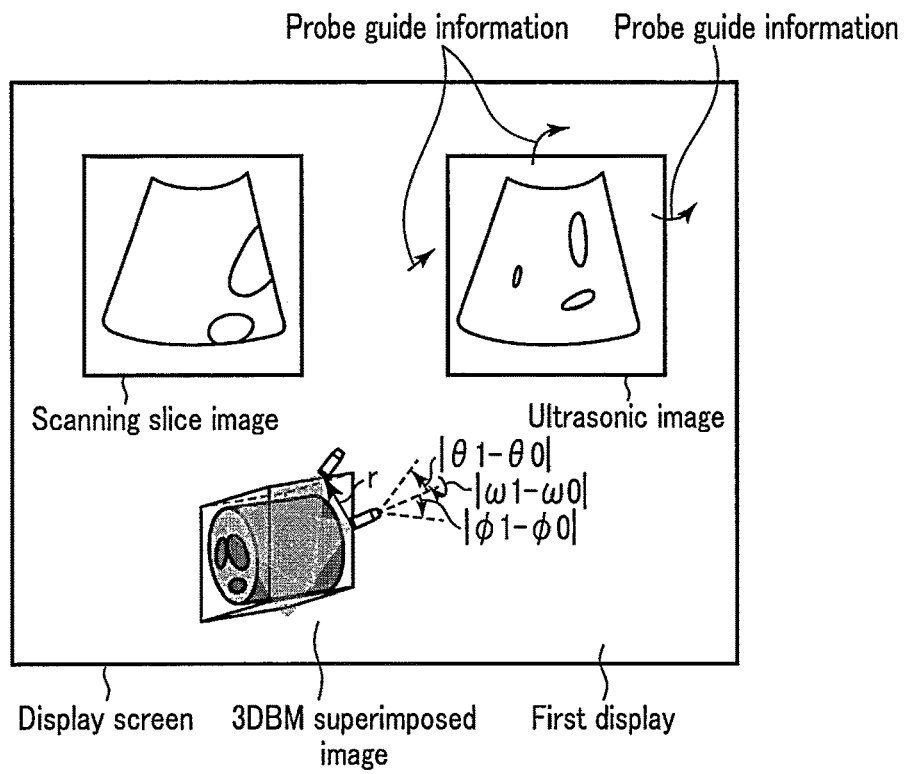
FIG. 8 is a view showing an example in which the probe guide information is superimposed on the ultrasonic image in the first display according to the first embodiment.
Figure 9:
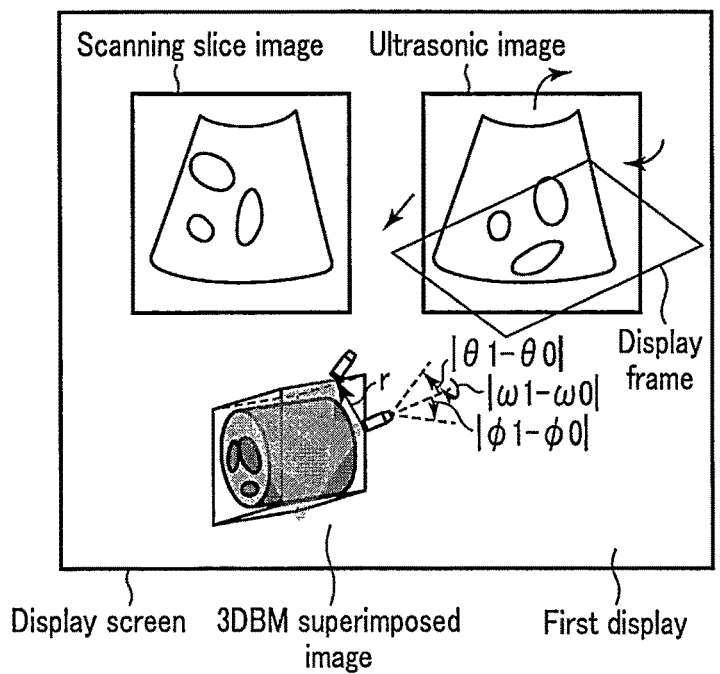
FIG. 9 is a view showing an example in which the probe guide information and the display frame of a scanning slice image are superimposed on the ultrasonic image in the first display according to first embodiment.

Note that when a thumbnail designation operation is executed, the display unit 19 may superimpose and display the probe guide information on the ultrasonic image. FIG. 8 is a view showing an example of the display screen on which the probe guide information is superimposed on the ultrasonic image in the first display. The display unit 19 may superimpose and display the display frame of the scanning slice image corresponding to the thumbnail image on the ultrasonic image in the first display. FIG. 9 is a view showing an example of the display screen on which the probe guide information and the display frame of the scanning slice image are superimposed and displayed on the ultrasonic image in the first display. The shape of the display frame is determined by, for example, the guide information generation unit 25 based on the designation position and probe position.

Furthermore, the display 19 can display the three-dimensional body mark image in accordance with the plurality of angles at the probe position. The display unit 19 can fix the probe position during scanning on the three-dimensional body mark image, and display the three-dimensional body mark image by rotating it by a predetermined angle.

(Probe Guide Information Display Function)

A probe guide information display function is a function of displaying the 3DBM superimposed image indicating the probe position and designation position together with the scanning slice image corresponding to the designated thumbnail image and the ultrasonic image during scanning. The processing (to be referred to as probe guide information display processing) of the probe guide information display function will be described below.

Figure 10:
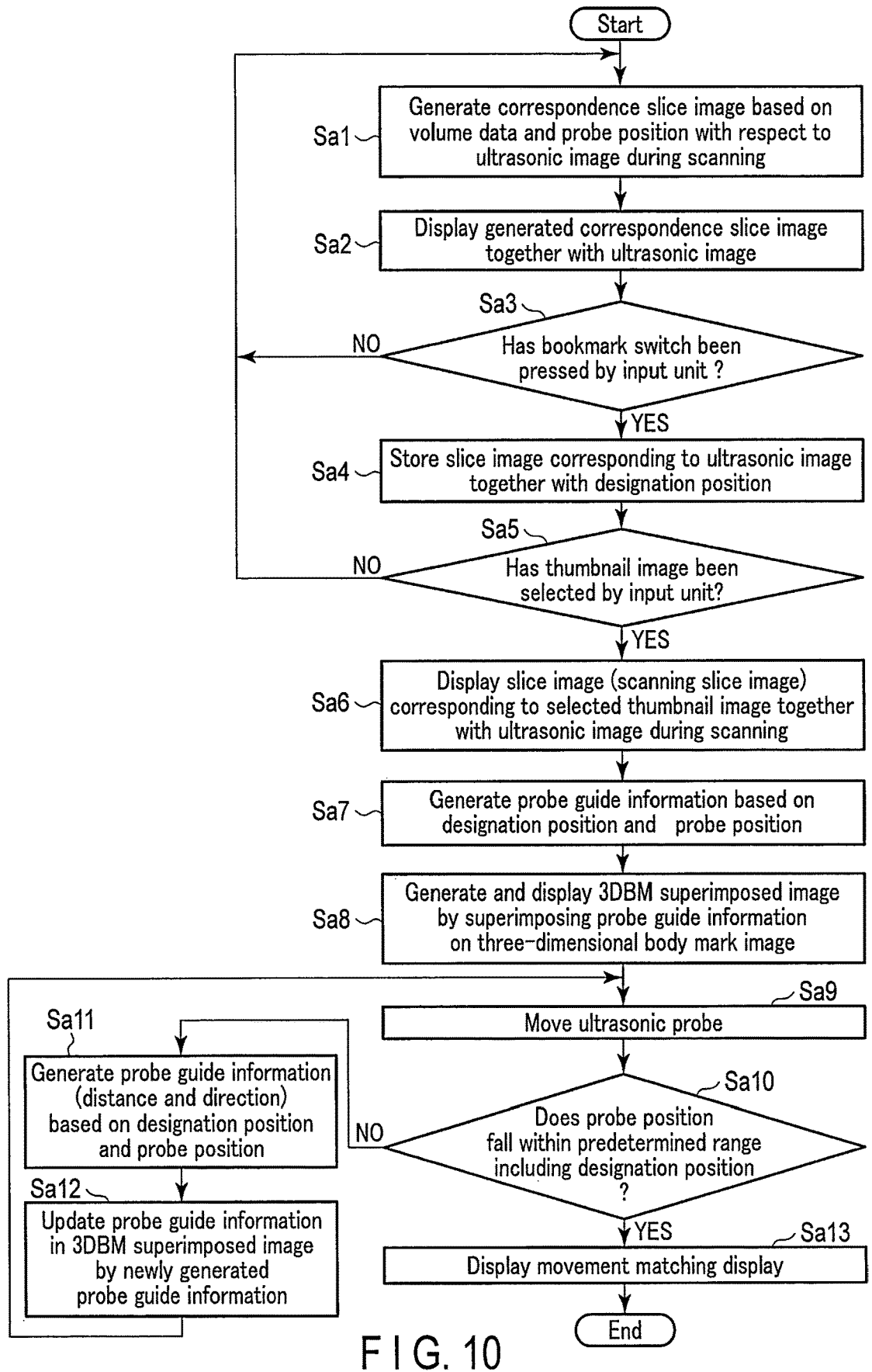
FIG. 10 is an example of a flowchart illustrating the processing procedure of a probe guide information display function according to the first embodiment.

FIG. 10 is an example of a flowchart illustrating the procedure of the probe guide information display processing.

When a dual display operation is executed, a correspondence slice image is generated based on the probe position with respect to the ultrasonic image during scanning and the volume data stored in the storage unit 29 (step Sa1). The generated correspondence slice image and the ultrasonic image during scanning are parallelly displayed (step Sa2). If no bookmark instruction is input via the input unit 18 (step Sa3), the processes in steps Sa1 and Sa2 are repeated. In this case, the correspondence slice image and the ultrasonic image corresponding to the probe position are repeatedly displayed on the display screen of the monitor of the display unit 19 in accordance with the movement of the ultrasonic probe 11.

If a bookmark instruction is input via the input unit 18 (the bookmark button is pressed) (step Sa3), a bookmark image and a slice image (scanning slice image) corresponding to the bookmark image are stored in the storage unit 29 together with the probe position (designation position) (step Sa4). At this time, a thumbnail image of the scanning slice image is generated, and displayed on the display screen of the monitor of the display unit 19. The processes in steps Sa1 to Sa4 are repeated until a thumbnail image is designated via the input unit 18 (a thumbnail designation operation is input) (step Sa5). At this time, a plurality of thumbnail images corresponding to a plurality of times of pressing of the bookmark button are displayed.

If a thumbnail image is designated via the input unit 18 (a thumbnail designation operation is input), the scanning slice image and designation position corresponding to the thumbnail image are read out from the storage unit 29. The readout scanning slice image is displayed together with the ultrasonic image during scanning (step Sa6). Probe guide information is generated based on the designation position and the probe position corresponding to the ultrasonic image during scanning. A 3DBM superimposed image is generated by superimposing the probe guide information on the three-dimensional body mark image, and displayed (step Sa8). The ultrasonic probe 11 is moved (step Sa9).

If the probe position falls outside the predetermined range including the designation position (step Sa10), probe guide information is newly generated based on the designation position and the probe position of the moved ultrasonic probe 11 (step Sa11). The probe guide information in the 3DBM superimposed image is updated (step Sa12).

If the probe position falls within the predetermined range including the designation position (step Sa10), the movement matching display is displayed (step Sa13). Note that if another thumbnail image is selected after the processing in step Sa13, the processes in steps Sa6 to Sa13 are repeated.

(First Modification)

The difference from the first embodiment is that when the probe position is moved into the predetermined range including the designation position, a plurality of slice images with respect to the designation position are generated based on the designation position and volume data, and the plurality of generated slice images are displayed together with the ultrasonic image during scanning. In this modification, there are a plurality of processes subsequent to step Sa13 in the probe guide information display processing according to the first embodiment.

By using movement matching as a trigger, the slice image generation unit 27 generates a plurality of slice images including slices whose positions are different from that of the slice of the scanning slice image based on the designation position and volume data. More specifically, the slice image generation unit 27 generates, as a plurality of slice images, a plurality of MPR (Multiplanar Reconstruction) images by executing MPR for the scanning slice image. By using movement matching as a trigger, the slice image generation unit 27 may generate a matching superimposed image by superimposing the ultrasonic image during scanning on the scanning slice image. The slice image generation unit 27 may read out an annotation about the scanning slice image from the storage unit 29, and generate an annotation superimposed image by superimposing the readout annotation on the ultrasonic image during scanning.

The display unit 19 displays the plurality of MPR images together with the ultrasonic image during scanning by using movement matching as a trigger. Display of the plurality of MPR images and the ultrasonic image during scanning will be referred to as the second display hereinafter. Note that the second display may further include a Doppler image. Note that the display unit 19 may display the matching superimposed image by using movement matching as a trigger. The display unit 19 may display the annotation superimposed image by using movement matching as a trigger. Note that the display unit 19 may display at least one of the first display and the second display.

The CPU 33 controls the display unit 19 to switch display of the monitor of the display unit 19 from the first display to the second display by using movement matching as a trigger. Note that the CPU 33 may control the display unit 19 to switch display of the monitor from the first display to display of the matching superimposed image by using movement matching as a trigger.

Figure 11:
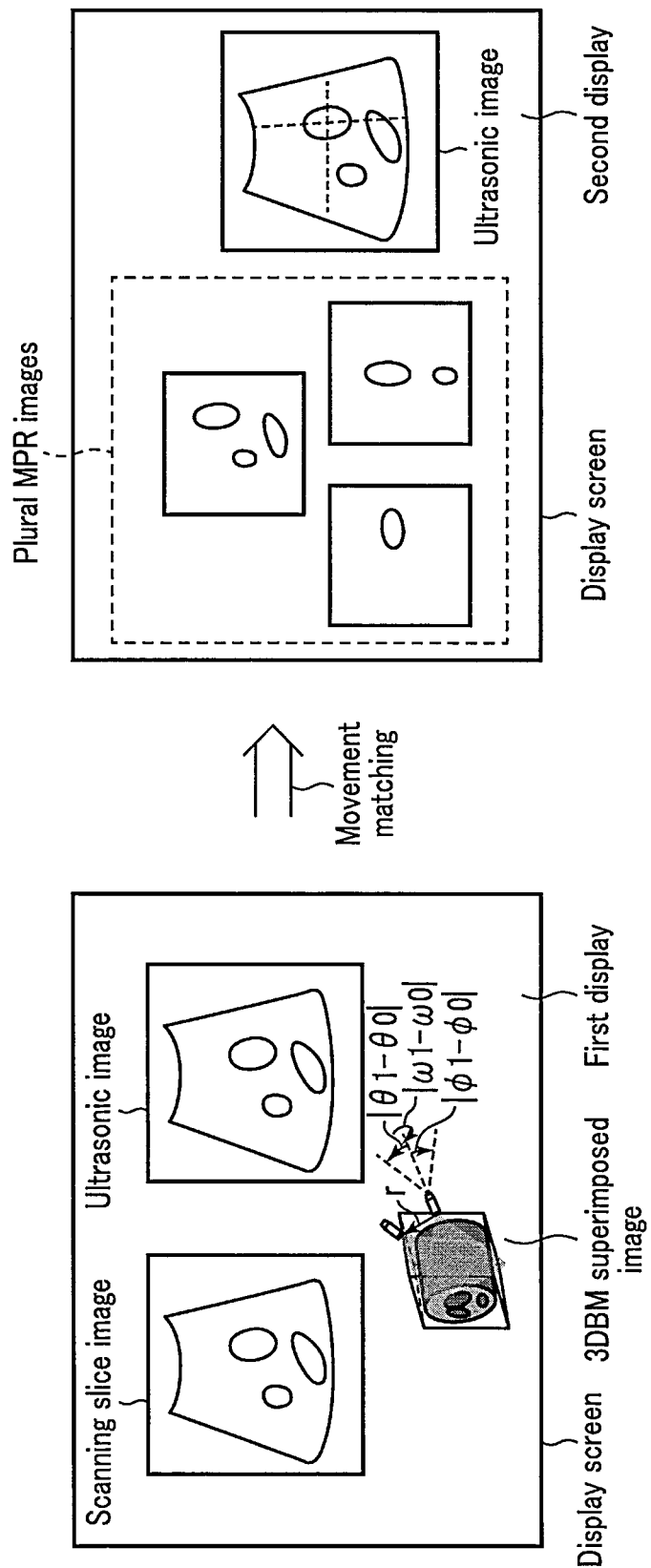
FIG. 11 is a view showing an example of the display screen whose display contents are switched from the first display to the second display by using, as a trigger, the movement of a probe position into a predetermined range corresponding to a designation position according to the first modification of the first embodiment.

FIG. 11 is a view showing an example of the display screen whose display contents are switched from the first display to the second display by using movement matching as a trigger. As shown in FIG. 11, in this modification, the display contents of the display screen are switched from the first display to the second display by using movement matching as a trigger.

Figure 12:
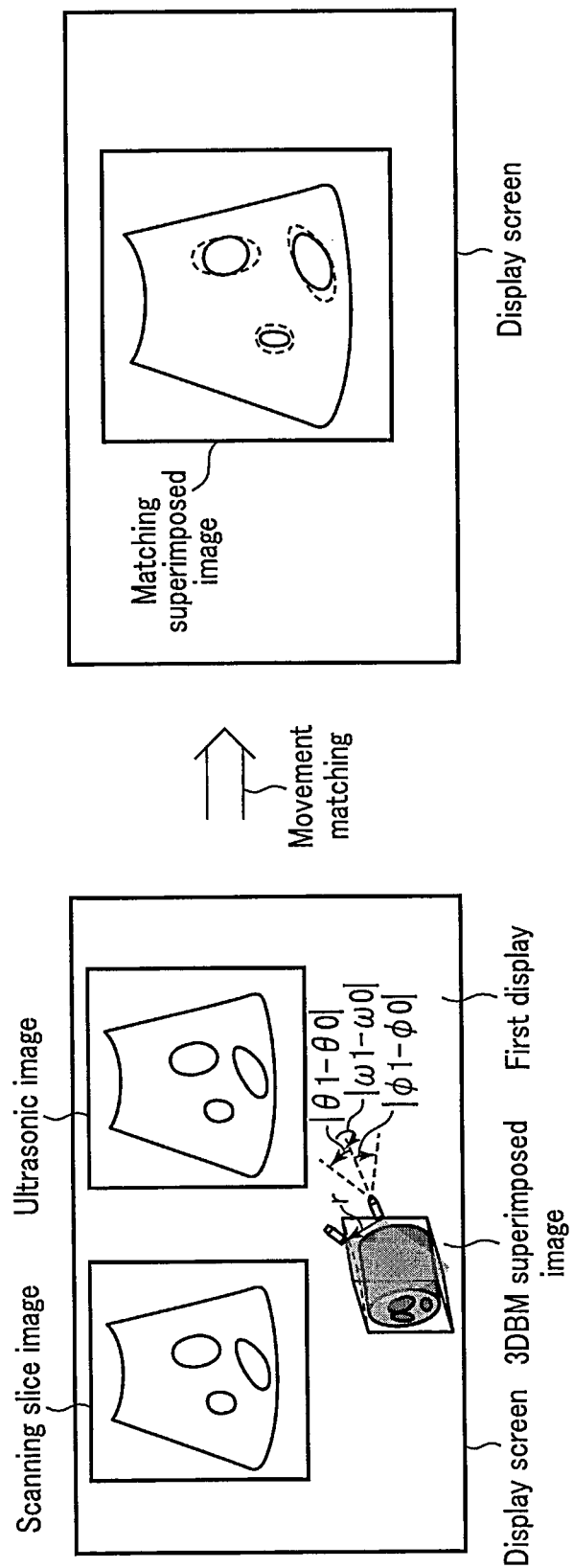
FIG. 12 is a view showing an example of the display screen whose display contents are switched from the first display to display of a matching superimposed image by using, as a trigger, the movement of the probe position into the predetermined range corresponding to the designation position according to the first modification of the first embodiment.

FIG. 12 is a view showing an example of the display screen whose display contents are switched from the first display to display of the matching superimposed image by using movement matching as a trigger.

Figure 13:
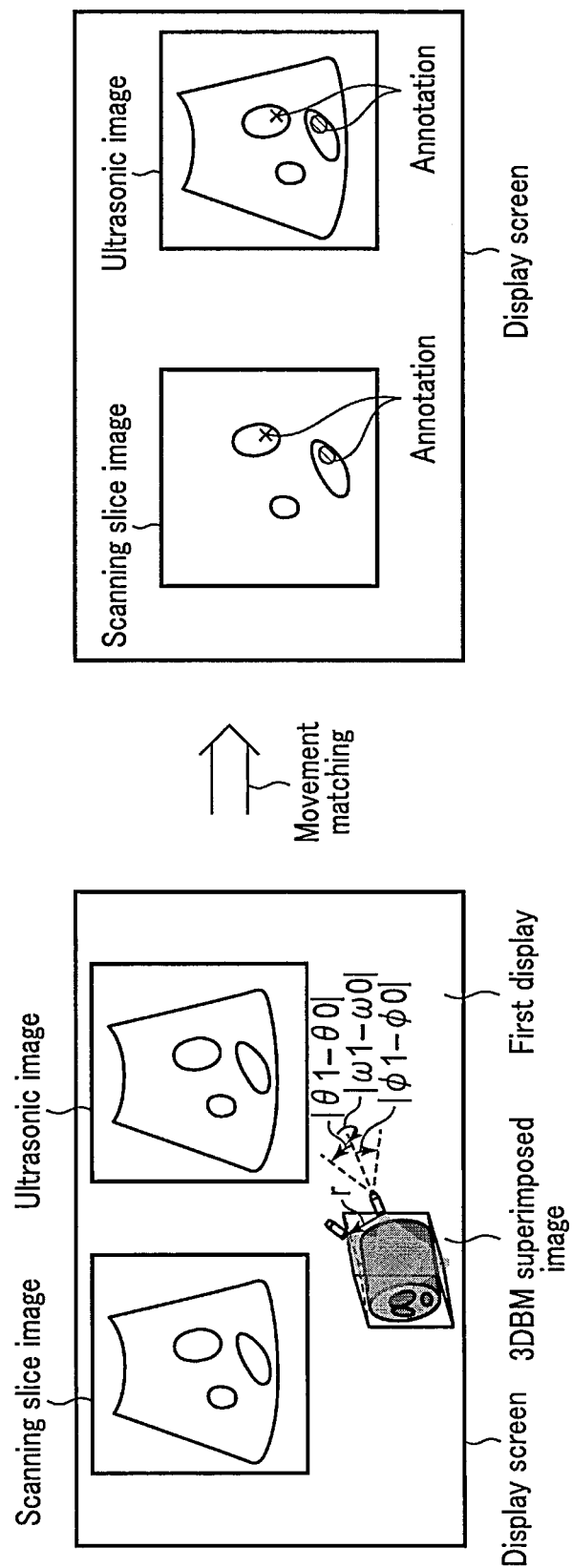
FIG. 13 is a view showing an example of the display screen whose display contents are switched from the first display to display of an annotation superimposed image by using, as a trigger, the movement of the probe position into the predetermined range corresponding to the designation position according to the first modification of the first embodiment.

FIG. 13 is a view showing an example of the display screen whose display contents are switched from the first display to display of the annotation superimposed image by using movement matching as a trigger.

(Display Switching Function)

A display switching function is a function of switching the display contents of the display screen from the first display to the second display by using, as a trigger, entering of the probe position into the predetermined range including the designation position (movement matching). The processing (to be referred to as display switching processing hereinafter) of the display switching function will be described below.

FIG. 14 is an example of a flowchart illustrating the procedure of the display switching processing.

In the first display, the probe position is moved into the predetermined range including the designation position along with the movement of the ultrasonic probe 11 (step Sb1). A plurality of slice images (MPR images) are generated based on the volume data and designation position (step Sb2). The CPU 33 controls switching of the display contents of the display screen from the first display to the second display (step Sb3). The plurality of generated slice images (MPR images) are displayed together with the ultrasonic image during scanning (step Sb4).

(Second Modification)

The difference from the first embodiment is that when the probe position is moved into the predetermined range including the designation position or the position corresponding to the designated slice, an ultrasonic scanning mode for the object is changed. In this modification, a plurality of processes subsequent to step Sa13 in the probe guide information display processing according to the first embodiment are included.

In this modification, assume that a two-dimensional array probe or a mechanical four-dimensional probe which executes three-dimensional scanning by swinging a one-dimensional array in a direction perpendicular to the array direction of the plurality of transducers is used as the ultrasonic probe 11.

The storage unit 29 stores a plurality of scanning modes. The plurality of scanning modes include a two-dimensional scanning mode of two-dimensionally scanning the object, and a three-dimensional scanning mode of three-dimensionally scanning the object. More specifically, the storage unit 29 stores a plurality of reception delay patterns with different focus depths, plurality of transmission delay patterns, and apparatus control programs with respect to the two-dimensional scanning mode. The storage unit 29 stores a plurality of reception delay patterns with different focus depths, a plurality of transmission delay patterns, and apparatus control programs with respect to the three-dimensional scanning mode.

The CPU 33 controls the scan unit 20 to change the scanning mode from the two-dimensional scanning mode to the three-dimensional scanning mode by using movement matching as a trigger. More specifically, the CPU 33 controls the scan unit 20 to execute the two-dimensional scanning mode until the probe position is moved into the predetermined range including the designation position. When the probe position is moved into the predetermined range including the designation position or the position corresponding to the designated slice, the CPU 33 controls the scan unit 20 to change the scanning mode from the two-dimensional scanning mode to the three-dimensional scanning mode. That is, the CPU 33 controls the scan unit 20 to execute the three-dimensional scanning mode after the movement of the probe position into the predetermined range including the designation position.

The CPU 33 controls the scan unit 20 to generate three-dimensional ultrasonic data by performing three-dimensional scanning on the object. By using movement matching as a trigger, the CPU 33 controls the slice image generation unit 27 to generate a plurality of ultrasonic images corresponding to the plurality of MPR images based on the three-dimensional ultrasonic data and the plurality of MPR images. By using movement matching as a trigger, the CPU 33 controls the display unit 19 to display the plurality of MPR images and the plurality of ultrasonic images.

The scan unit 20 scans the object according to the scanning mode set by the CPU 33. More specifically, if the two-dimensional scanning mode is set, the scan unit 20 executes two-dimensional ultrasonic scanning on the object. If the three-dimensional scanning mode is set, the scan unit 20 executes three-dimensional ultrasonic scanning (a volume scan) on the object. The scan unit 20 generates three-dimensional ultrasonic data by performing a volume scan on the object.

The slice image generation unit 27 generates a plurality of ultrasonic images corresponding to the plurality of MPR images based on the three-dimensional volume data and the plurality of MPR images by using movement matching as a trigger.

The display unit 19 displays the plurality of ultrasonic images corresponding to the plurality of MPR images by using movement matching as a trigger.

(Scanning Mode Change Function)

A scanning mode change function is a function of changing the ultrasonic scanning mode for the object when the probe position is moved into the predetermined range including the designation position or the position corresponding to the designated slice. The processing (to be referred to as scanning mode change processing hereinafter) of the scanning mode change function will be described below.

Figure 15:
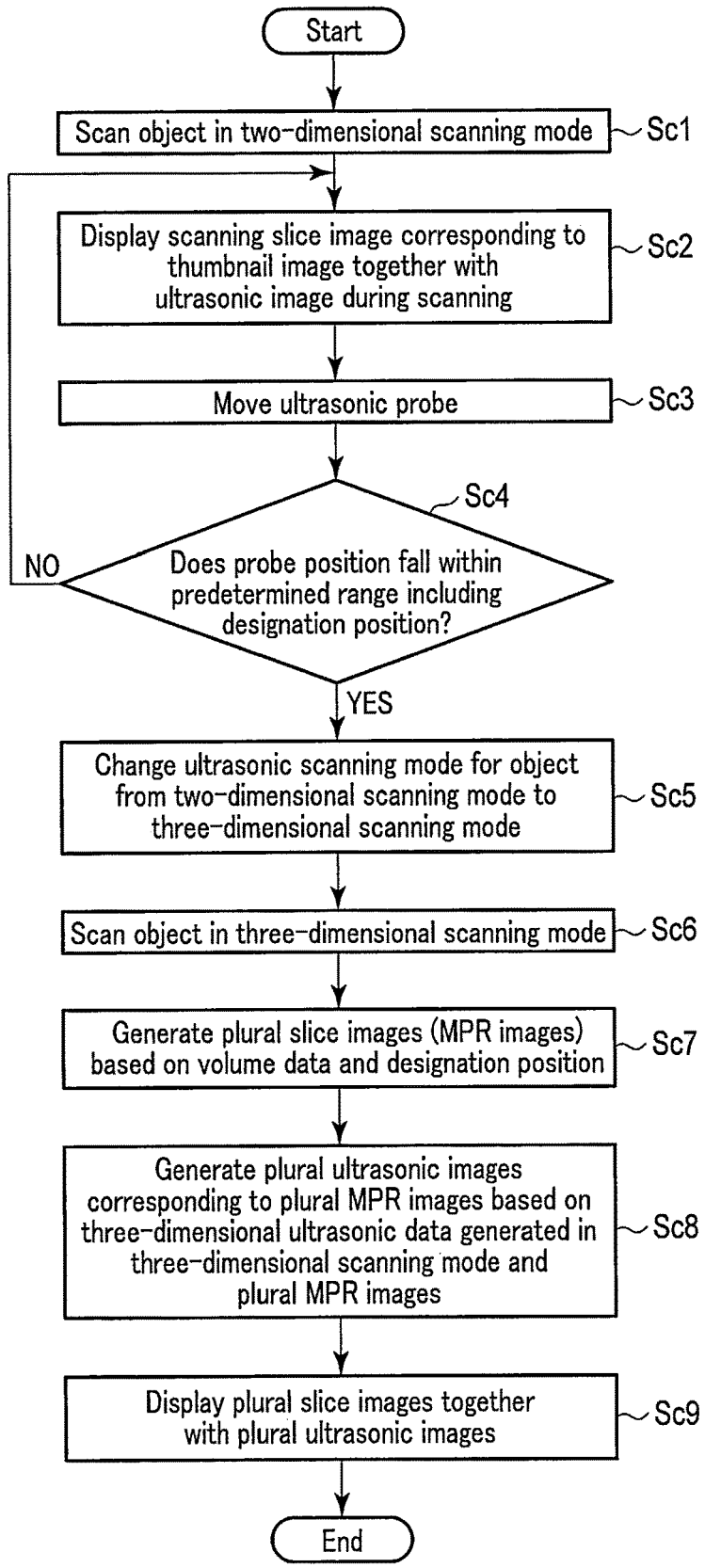
FIG. 15 is a flowchart illustrating an example of a procedure of changing a scanning mode by using, as a trigger, the movement of the probe position into the predetermined range corresponding to the designation position according to the second modification of the first embodiment.

FIG. 15 is an example of a flowchart illustrating the procedure of the scanning mode changing processing.

In the two-dimensional scanning mode, the object is scanned (step Sc1). When a dual display operation is executed, a correspondence slice image is generated based on the probe position with respect to the ultrasonic image during scanning and the volume data stored in the storage unit 29. The generated correspondence slice image and the ultrasonic image during scanning are parallelly displayed. When a bookmark instruction is input via the input unit 18 (the bookmark button is pressed), a bookmark image and a slice image (scanning slice image) corresponding to the bookmark image are stored in the storage unit 29 together with the probe position (designation position). At this time, a thumbnail image of the scanning slice image is generated, and displayed on the display screen of the monitor of the display unit 19.

When a thumbnail image is designated via the input unit 18 (a thumbnail designation operation is input), a scanning slice image corresponding to the thumbnail image and the designation position (or the position corresponding to the designated slice) are read out from the storage unit 29. The readout scanning slice image is displayed together with the ultrasonic image during scanning (step Sc2). Probe guide information is generated based on the designation position (or the position corresponding to the designated slice) and the probe position corresponding to the ultrasonic image during scanning. A 3DBM superimposed image is generated by superimposing the probe guide information on the three-dimensional body mark image, and displayed. The ultrasonic probe 11 is moved (step Sc3).

If the probe position falls outside the predetermined range including the designation position (or the position corresponding to the designated slice) (step Sc4), new probe guide information is generated based on the probe position of the moved ultrasonic probe 11 and the designation position (or the position corresponding to the designated slice). The probe guide information in the 3DBM superimposed image is updated. Subsequently, the processes in steps Sc2 and Sc3 are executed.

If the probe position falls within the predetermined range including the designation position (or the position corresponding to the designated slice) (step Sc4), the ultrasonic scanning mode for the object is changed from the two-dimensional scanning mode to the three-dimensional scanning mode (step Sc5). In the three-dimensional scanning mode, the object is scanned (step Sc6). A plurality of slice images (MPR images) are generated based on the volume data and the designation position (or the position corresponding to the designated slice) (step Sc7).

A plurality of ultrasonic images corresponding to the plurality of MPR images are generated based on the three-dimensional ultrasonic data and the plurality of MPR images (step Sc8). The plurality of slice images are displayed together with the plurality of ultrasonic images (step Sc9).

With the above-described arrangement, it is possible to obtain the following effects.

The ultrasonic diagnostic apparatus 1 according to this embodiment has the probe guide information display function of displaying again the ultrasonic image stored in advance by the operator. The ultrasonic diagnostic apparatus 1 can generate probe guide information based on the difference information between the designation position (the position (coordinates) in the three-dimensional space and the three-axis rotation directions) of the stored ultrasonic image, and display the probe guide information. This enables the ultrasonic diagnostic apparatus 1 to directly guide the operator to the designation position with respect to the desired scanning slice. That is, the ultrasonic diagnostic apparatus 1 can efficiently guide a position, at which the ultrasonic probe 11 is brought into contact with the object, to the position of the ultrasonic probe with respect to the scanning slice desired by the operator.

According to the first modification of the embodiment, when the probe position is moved into the predetermined range including the designation position, it is possible to generate a plurality of slice images with respect to the designation position based on the designation position and volume data, and display the plurality of generated slice images together with the ultrasonic image during scanning. That is, according to the first modification, the display contents displayed on the display screen can be changed from the first display to the second display by using movement matching as a trigger. This makes it possible to display the plurality of slice images when the ultrasonic image almost matches the scanning slice image.

According to the second modification of the embodiment, it is possible to change the ultrasonic scanning mode for the object by using movement matching as a trigger. Thus, it is possible to generate a plurality of ultrasonic images corresponding to the plurality of slice images (MPR images) in the second display.

As described above, the ultrasonic diagnostic apparatus 1 can efficiently guide a position, at which the ultrasonic probe 11 is brought into contact with the object, to the designation position (or the position corresponding to the designated slice). By using movement matching as a trigger, the ultrasonic diagnostic apparatus 1 can also change the display contents displayed on the display screen from the first display to the second display. In addition, the ultrasonic diagnostic apparatus 1 can change the ultrasonic scanning mode for the object by using movement matching as a trigger. Consequently, with the ultrasonic diagnostic apparatus 1, the diagnosis efficiency of the operator for the object is improved.

Second Embodiment

The difference from the first embodiment is that a program (to be referred to as an image processing program hereinafter) for a predetermined image display processing function is activated by using, as a trigger, the movement of a probe position into a predetermined range including a designation position, and predetermined image processing is executed.

Figure 16:
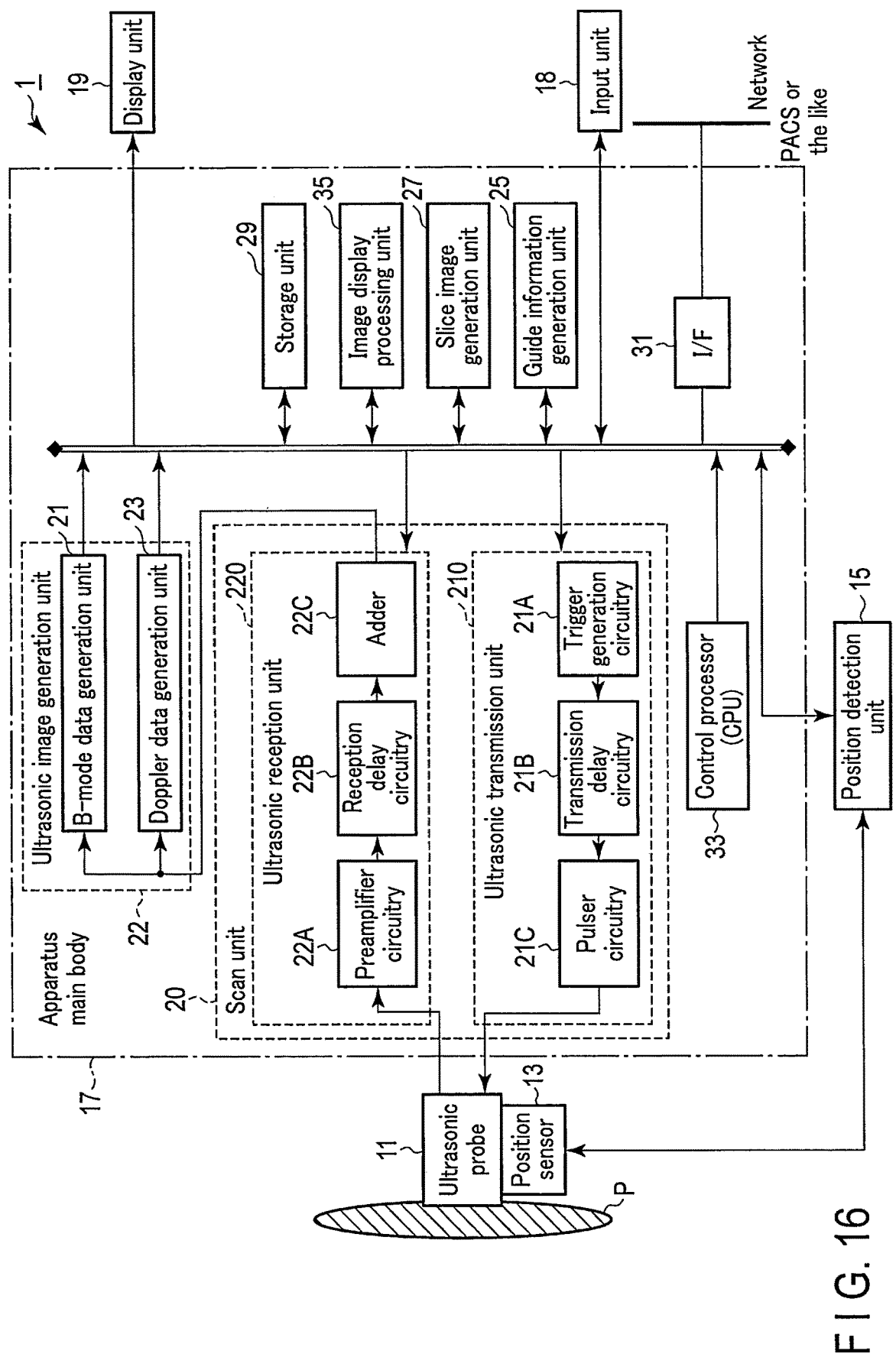
FIG. 16 is a view showing an example of the arrangement of an ultrasonic diagnostic apparatus according to the second embodiment.

FIG. 16 is a view showing an example of the arrangement of an ultrasonic diagnostic apparatus 1 according to the second embodiment.

The ultrasonic diagnostic apparatus includes an image display processing unit 35 in addition to the respective units of the ultrasonic diagnostic apparatus 1 according to the first embodiment.

Storage unit 29 stores a predetermined image processing program. The storage unit 29 outputs the predetermined image processing program to the image display processing unit 35 by using movement matching as a trigger.

The image display processing unit 35 executes predetermined image display processing for a plurality of images in the second display by using movement matching as a trigger. More specifically, the image display processing unit 35 superimposes the insertion path of a puncture needle on an ultrasonic image in the second display by using movement matching as a trigger. For example, the insertion path of the puncture needle may be input in advance via input unit 18.

The image display processing unit 35 superimposes a predetermined measurement tool on the ultrasonic image in the second display by using movement matching as a trigger. More specifically, the image display processing unit 35 superimposes a marker (to be referred to as a measurement marker) associated with predetermined measurement on a predetermined tissue region in the ultrasonic image in the second display. The measurement marker is, for example, a calliper for measuring the distance between two points on the ultrasonic image, a marker for measuring the area within the measurement marker, or the like. Note that the image display processing unit 35 can also superimpose, on the second display, a measurement result by the measurement marker displayed on the ultrasonic image.

The image display processing unit 35 stores a predetermined extraction threshold associated with region extraction processing in a memory (not shown). By using movement matching as a trigger, the image display processing unit 35 executes region extraction processing (segmentation processing) for the ultrasonic image in the second display using the predetermined extraction threshold. The image display processing unit 35 superimposes and displays the processing result of the segmentation processing on the ultrasonic image in the second display.

By using movement matching as a trigger, a display unit 19 displays an image obtained by executing the predetermined image display processing for the plurality of images in the second display. More specifically, by using movement matching as a trigger, the display unit 19 displays an image obtained by superimposing the insertion path of the puncture needle on the ultrasonic image in the second display.

Figure 17:
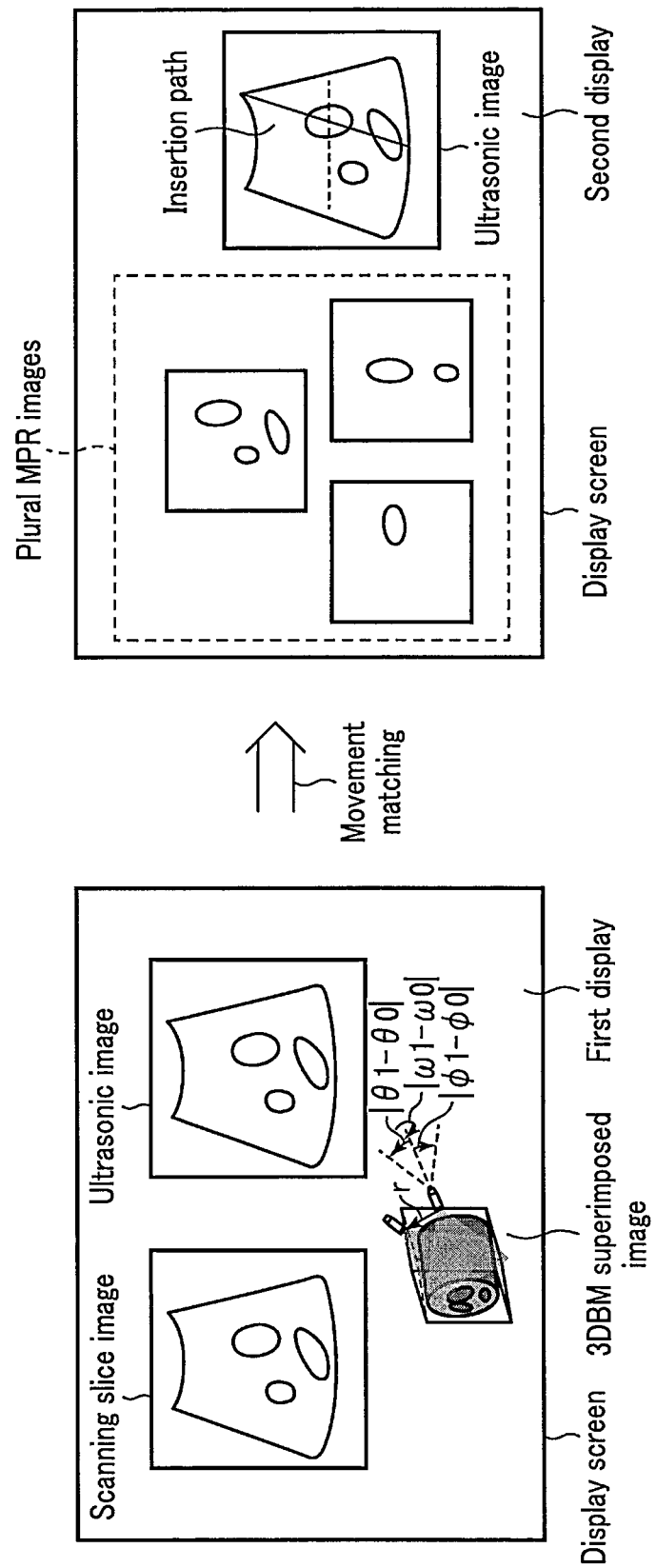
FIG. 17 is a view showing an example of display of the insertion path of a puncture needle on an ultrasonic image by using, as a trigger, the movement of a probe position into a predetermined range corresponding to a designation position according to the second embodiment.

FIG. 17 is a view showing an example in which the insertion path of the puncture needle is displayed on the ultrasonic image by using, as a trigger, entering of the probe position into the predetermined range including the designation position. As shown in FIG. 17, the insertion path of the puncture needle is displayed on the ultrasonic image in the second display by using a movement matching as a trigger. Note that the display unit 19 may superimpose and display the insertion path of the puncture needle on an MPR image corresponding to the ultrasonic image in the second display.

Figure 18:
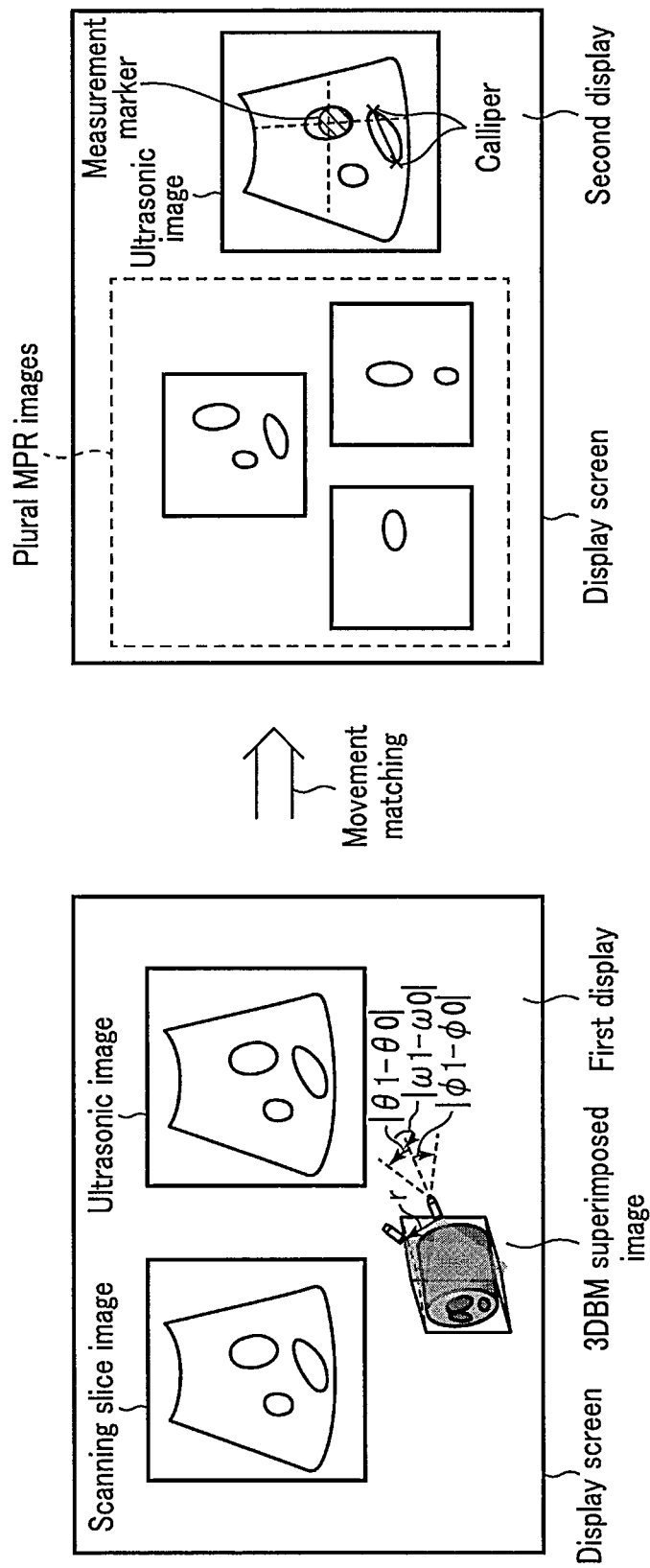
FIG. 18 is a view showing an example in which a marker associated with predetermined measurement is displayed on the ultrasonic image by using, as a trigger, the movement of the probe position into the predetermined range corresponding to the designation position according to the second embodiment.

The display unit 19 superimposes and displays the measurement marker on the ultrasonic image in the second display by using movement matching as a trigger. FIG. 18 is a view showing an example in which the measurement tool is displayed on the ultrasonic image by using, as a trigger, entering of the probe position into the predetermined range including the designation position. As shown in FIG. 18, the display unit 19 superimposes and displays the calliper and measurement marker on the tissue region displayed in the ultrasonic image in the second display.

Figure 19:
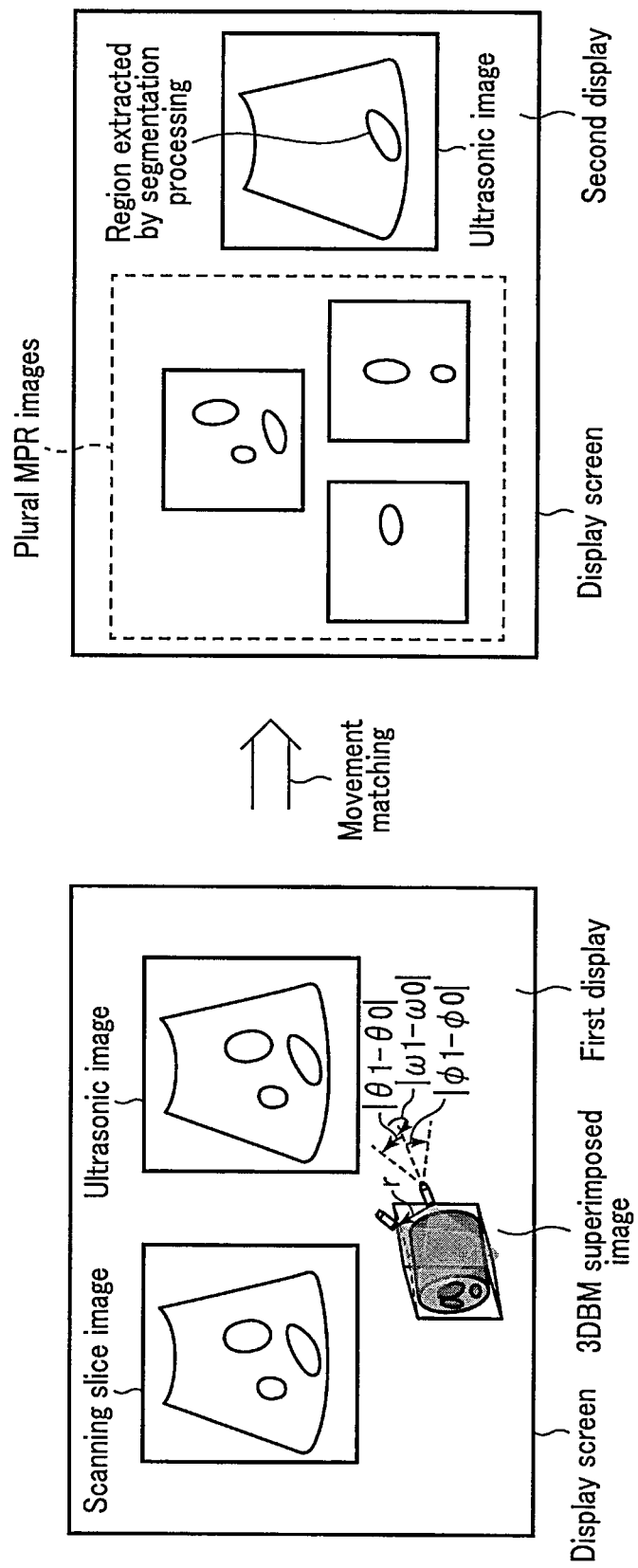
FIG. 19 is a view showing an example of display by extracting a predetermined tissue region in the ultrasonic image in the second display by using, as a trigger, the movement of the probe position into the predetermined range corresponding to the designation position according to the second embodiment.
Figure 21:
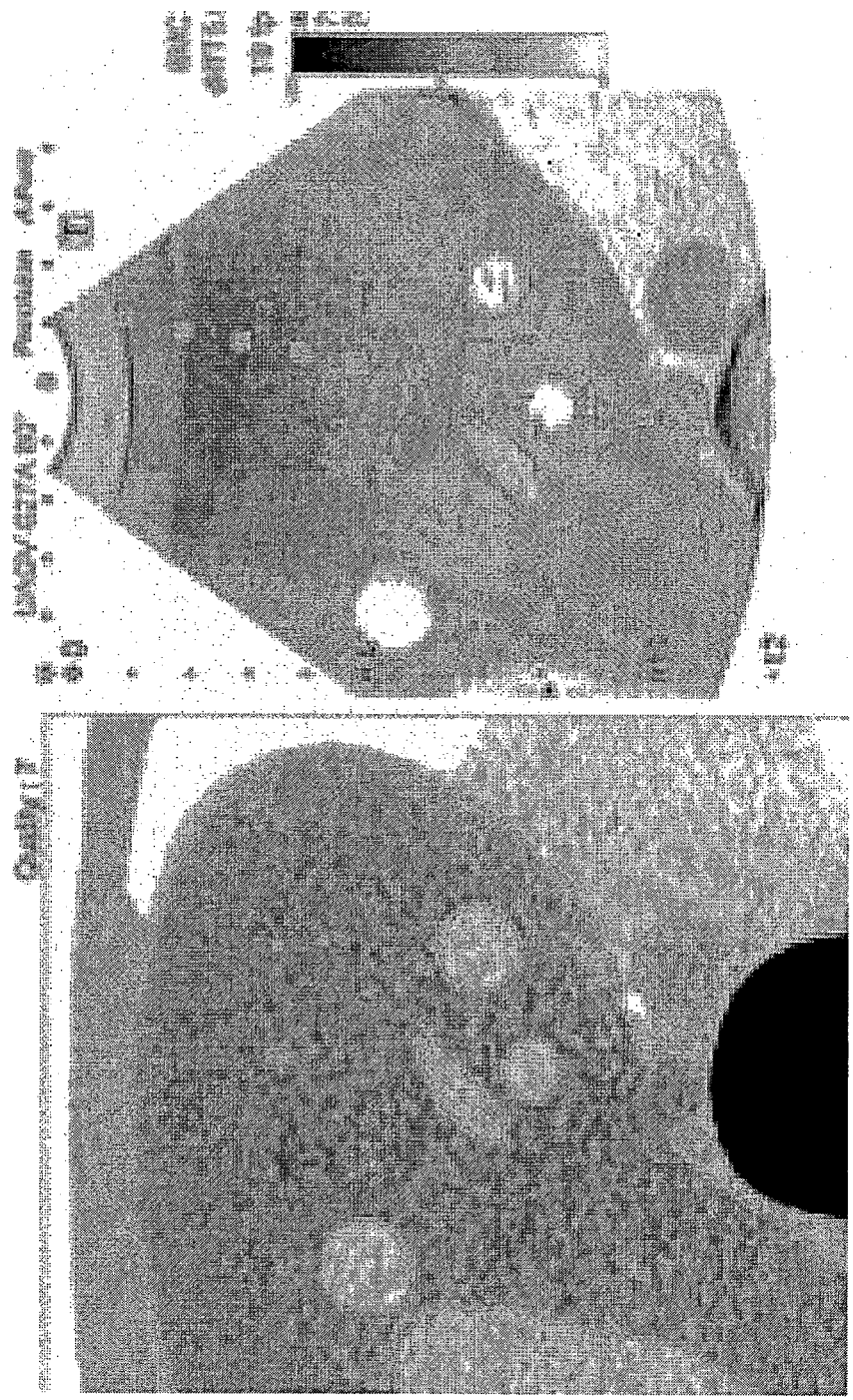
FIG. 21 is a view showing display of two slice images obtained by different modalities according to the conventional technique.
Figure 22:
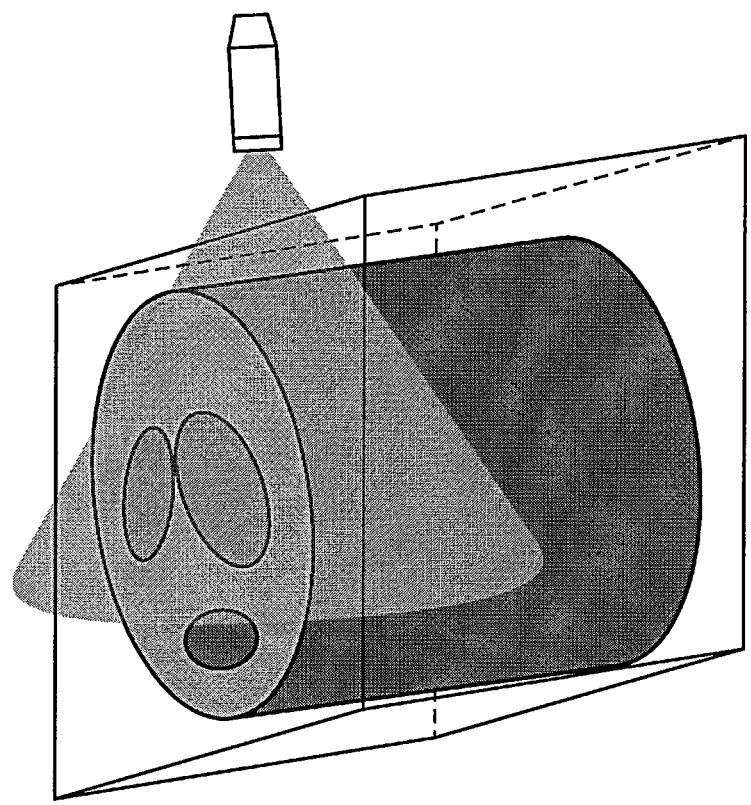
FIG. 22 is a view showing a three-dimensional body mark according to the conventional technique.

By using movement matching as a trigger, the display unit 19 displays the ultrasonic image for which the segmentation processing has been executed using the predetermined extraction threshold. FIG. 19 is a view showing an example of the second display by extracting the predetermined tissue region from the ultrasonic image in the second display by using, as a trigger, entering of the probe position into the predetermined range including the designation position.

(Image Display Processing Function)

By using movement matching as a trigger, the image display processing function reads out the predetermined image processing program, activates the readout program, and executes the predetermined image display processing for the ultrasonic image in the second display. The predetermined image display processing is, for example, the processing of superimposing the insertion path of the puncture needle, the measurement tool display processing, the processing of displaying the measurement result by the measurement tool, the segmentation processing, or the like. The processing of the image display processing function will be referred to as image display processing hereinafter.

FIG. 20 is a flowchart illustrating an example of the procedure of the image display processing.

The image processing program is read out from the storage unit 29 by using a movement matching as a trigger (step Sd1). The image display processing is executed for the ultrasonic image in the second display according to the readout image processing program (step Sd2). Note that the target of the image display processing may be the plurality of slice images (MPR images) in the second display. In the second display, the image having undergone the image display processing is displayed (step Sd3).

With the above-described arrangement, it is possible to obtain the following effects.

The ultrasonic diagnostic apparatus 1 according to this embodiment can automatically execute the predetermined image display processing by using, as a trigger, entering of the probe position into the predetermined range including the designation position (movement matching). That is, in the ultrasonic diagnostic apparatus 1, the image display processing program is activated to execute the predetermined image display processing without activating the image display processing program by the operator. Consequently, the ultrasonic diagnostic apparatus can improve the diagnosis and treatment efficiency, resulting in improvement of detailed examination throughput and the like.

Therefore, the ultrasonic diagnostic apparatus 1 can improve the reproducibility and efficiency of optimum treatment slice display as a preparation to, for example, ultrasonically guided treatment, thereby reducing the loads on the operator and object.

In addition, each function according to the embodiments can be implemented by installing a program for executing the processing in a computer such as a work station, and loading it onto a memory. In this case, it is possible to store the program capable of causing the computer to execute the method in a storage medium such as a magnetic disk (a hard disk or the like), an optical disk (a CD-ROM, a DVD, or the like), or a semiconductor memory, and distribute it.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
an ultrasonic probe configured to transmit an ultrasonic wave to an object and receive a reflected wave from the object;
a position detector configured to detect a probe position of the ultrasonic probe; and
processing circuitry configured to:
generate an ultrasonic image based on the received reflected wave,
store previously acquired volume data of the object and a designation position on the previously acquired volume data designated by an operator in association with each other,
generate a slice image corresponding to the designation position based on the previously acquired volume data and the designation position,
display at least one of a first content displaying the slice image and the ultrasonic image, and a second content displaying at least the ultrasonic image and display contents different from display contents in the first content,
control switching from the first content to the second content in response to movement of the probe position detected by the position detector into a range corresponding to the designation position,
execute a predetermined image display processing function on the ultrasonic image in the second content in response to movement of the probe position into the range,
scan the object in a plurality of scanning modes, and
change a scanning mode to be executed for the object from a two-dimensional scanning mode to a three-dimensional scanning mode in response to movement of the probe position into the range.

2. The ultrasonic diagnostic apparatus according to claim 1, wherein the designation position is related to the probe position.

3. The ultrasonic diagnostic apparatus according to claim 1, wherein the processing circuitry is further configured to:
generate, based on the designation position and the probe position, probe guide information including a distance between the probe position and the designation position, a direction from the probe position to the designation position, and an angle of the ultrasonic probe at the designation position, and
display the generated probe guide information together with the ultrasonic image in the first content.

4. The ultrasonic diagnostic apparatus according to claim 1, wherein the processing circuitry is further configured to display the first content when the probe position falls outside the range, and display the second content when the probe position falls within the range.

5. The ultrasonic diagnostic apparatus according to claim 1, wherein the image display processing function is a function of displaying an insertion path of a puncture needle on the ultrasonic image in the second content.

6. The ultrasonic diagnostic apparatus according to claim 1, wherein the image display processing function is a function of displaying a marker associated with predetermined measurement on the ultrasonic image in the second content.

7. The ultrasonic diagnostic apparatus according to claim 1, wherein the image display processing function is a function of extracting and displaying a predetermined tissue region in the ultrasonic image in the second content based on the predetermined tissue region in the slice image and a predetermined threshold.

8. The ultrasonic diagnostic apparatus according to claim 1, wherein the processing circuitry is further configured to:
generate a superimposed image by superimposing the ultrasonic image on the slice image in the second content, and
display at least one of the first content and the superimposed image.

9. The ultrasonic diagnostic apparatus according to claim 1, wherein the processing circuitry is configured to:
generate a superimposed image by superimposing an annotation about the slice image on at least one of the slice image and the ultrasonic image in the second content, and
display at least one of the first display content and the superimposed image together with the ultrasonic image.

10. The ultrasonic diagnostic apparatus according to claim 1, wherein the processing circuitry is further configured to:
generate a superimposed image by superimposing a view position of the slice image on the ultrasonic image, and
display the superimposed image together with the slice image in the first content.

11. An ultrasonic diagnostic apparatus comprising:
an ultrasonic probe configured to transmit an ultrasonic wave to an object and receive a reflected wave from the object;
a position detector configured to detect a probe position of the ultrasonic probe; and
processing circuitry configured to:
- generate an ultrasonic image based on the received reflected wave,
- store a position corresponding to a designated slice position of the object and previously acquired volume data in association with each other,
- generate a thumbnail image corresponding to the designated slice position based on one of the previously acquired volume data or the ultrasonic image,
- generate probe guide information for guiding the ultrasonic probe from the probe position to the designated slice position based on the designated slice position with respect to the thumbnail image displayed on the display and designated via an input device, and the probe position detected by the position detector,
- execute a predetermined image display processing function on the ultrasonic image in response to movement of the probe position into a range corresponding to the designated slice position,
- display the probe guide information,
- scan the object in a plurality of scanning modes, and
- change a scanning mode to be executed for the object from a two-dimensional scanning mode to a three-dimensional scanning mode in response to movement of the probe position into the range corresponding to the designated slice position.

12. The ultrasonic diagnostic apparatus according to claim 11, wherein the designated slice position is related to the probe position.

13. An ultrasonic diagnostic apparatus comprising:
an ultrasonic probe configured to transmit an ultrasonic wave to an object and receive a reflected wave from the object;
a position detector configured to detect a probe position of the ultrasonic probe; and
processing circuitry configured to:
- store previously acquired volume data of the object and a designation position on the previously acquired volume data designated by an operator in association with each other,
- generate a slice image corresponding to the designation position and a plurality of slice images including a slice whose position is different from a position of a slice of the slice image based on the previously acquired volume data and the designation position,
- display at least one of a first content displaying the slice image and a second content displaying the slice images,
- control switching from the first content to the second content in response to movement of the probe position detected by the position detector into a range corresponding to the designation position,
- execute a predetermined image display processing function on the ultrasonic image in the second content in response to movement of the probe position into the range,
- scan the object in a plurality of scanning modes, and
- change a scanning mode to be executed for the object from a two-dimensional scanning mode to a three-dimensional scanning mode in response to movement of the probe position into the range.

* * * * *